US008836345B2

(12) United States Patent
Chetham et al.

(10) Patent No.: US 8,836,345 B2
(45) Date of Patent: Sep. 16, 2014

(54) IMPEDANCE DETERMINATION

(75) Inventors: Scott Chetham, Del Mar, CA (US);
Christopher Newton Daly, Newport (AU); Ian John Bruinsma, Kings Langley (AU)

(73) Assignee: Impedimed Limited, Pinkenba, Queensland (AU)

( * ) Notice: Subject to any disclaimer, the term of this patent is extended or adjusted under 35 U.S.C. 154(b) by 1010 days.

(21) Appl. No.: 12/741,368

(22) PCT Filed: Oct. 15, 2008

(86) PCT No.: PCT/AU2008/001521
§ 371 (c)(1),
(2), (4) Date: Oct. 21, 2010

(87) PCT Pub. No.: WO2009/059351
PCT Pub. Date: May 14, 2009

(65) Prior Publication Data
US 2011/0025348 A1 Feb. 3, 2011

(30) Foreign Application Priority Data

Nov. 5, 2007 (AU) ................................ 2007906049

(51) Int. Cl.
*G01R 27/28* (2006.01)
*A61B 5/053* (2006.01)
(52) U.S. Cl.
CPC ..................................... *A61B 5/053* (2013.01)
USPC ............ 324/649; 600/372; 600/509; 600/547
(58) Field of Classification Search
USPC ............ 324/649, 57, 408, 679; 600/372, 509, 600/547
See application file for complete search history.

(56) References Cited

U.S. PATENT DOCUMENTS

| 3,316,896 A | 5/1967 | Thomasset |
| 3,851,641 A | 12/1974 | Toole et al. |
| 3,871,359 A | 3/1975 | Pacela |

(Continued)

FOREIGN PATENT DOCUMENTS

| CA | 2231038 | 11/1999 |
| CA | 2638958 | 6/2000 |

(Continued)

OTHER PUBLICATIONS

International Search Report and Written Opinion of the International Searching Authority issued in in PCT/AU2008/001521 dated Jan. 15, 2009.

(Continued)

*Primary Examiner* — Huy Q Phan
*Assistant Examiner* — Giovanni Astacio-Oquendo
(74) *Attorney, Agent, or Firm* — Knobbe Martens Olson & Bear LLP

(57) ABSTRACT

Apparatus for use in performing impedance measurements on a subject. The apparatus includes a processing system for causing a first signal to be applied to the subject, determining an indication of a second signal measured across the subject, using the indication of the second signal to determine any imbalance and if an imbalance exists, determining a modified first signal in accordance with the imbalance and causing the modified first signal to be applied to the subject to thereby allow at least one impedance measurement to be performed.

45 Claims, 15 Drawing Sheets

(56) References Cited

U.S. PATENT DOCUMENTS

| | | | |
|---|---|---|---|
| 4,008,712 A | 2/1977 | Nyboer |
| 4,034,854 A | 7/1977 | Bevilacqua |
| 4,144,878 A | 3/1979 | Wheeler |
| 4,184,486 A | 1/1980 | Papa |
| 4,291,708 A | 9/1981 | Frei et al. |
| 4,314,563 A | 2/1982 | Wheeler |
| 4,353,372 A | 10/1982 | Ayer |
| 4,365,634 A | 12/1982 | Bare et al. |
| 4,407,288 A | 10/1983 | Langer et al. |
| 4,407,300 A | 10/1983 | Davis |
| 4,450,527 A | 5/1984 | Sramek |
| 4,458,694 A | 7/1984 | Sollish et al. |
| 4,468,832 A | 9/1984 | Batchelor |
| 4,486,835 A | 12/1984 | Bai et al. |
| 4,537,203 A | 8/1985 | Machida |
| 4,539,640 A | 9/1985 | Fry et al. |
| 4,557,271 A | 12/1985 | Stoller et al. |
| 4,583,549 A | 4/1986 | Manoli |
| 4,602,338 A | 7/1986 | Cook |
| 4,617,939 A | 10/1986 | Brown et al. |
| 4,646,754 A | 3/1987 | Seale |
| 4,686,477 A | 8/1987 | Givens et al. |
| 4,688,580 A | 8/1987 | Ko et al. |
| 4,763,660 A | 8/1988 | Kroll et al. |
| 4,793,362 A | 12/1988 | Tedner |
| 4,832,608 A | 5/1989 | Kroll |
| 4,895,163 A | 1/1990 | Libke et al. |
| 4,899,758 A | 2/1990 | Finkelstein et al. |
| 4,905,705 A | 3/1990 | Kizakevich et al. |
| 4,911,175 A | 3/1990 | Shizgal |
| 4,942,880 A | 7/1990 | Slovák |
| 4,951,682 A | 8/1990 | Petre |
| 4,981,141 A * | 1/1991 | Segalowitz ............ 600/509 |
| 5,025,784 A | 6/1991 | Shao et al. |
| 5,063,937 A | 11/1991 | Ezenwa et al. |
| 5,078,134 A | 1/1992 | Heilman et al. |
| 5,143,079 A | 9/1992 | Frei et al. |
| 5,197,479 A | 3/1993 | Hubelbank et al. |
| 5,199,432 A | 4/1993 | Quedens et al. |
| 5,246,008 A | 9/1993 | Mueller |
| 5,280,429 A | 1/1994 | Withers |
| 5,305,192 A | 4/1994 | Bonte et al. |
| 5,309,917 A | 5/1994 | Wang et al. |
| 5,311,878 A | 5/1994 | Brown et al. |
| 5,372,141 A | 12/1994 | Gallup et al. |
| 5,415,164 A | 5/1995 | Faupel |
| 5,449,000 A | 9/1995 | Libke et al. |
| 5,465,730 A | 11/1995 | Zadehkoochak et al. |
| 5,469,859 A | 11/1995 | Tsoglin et al. |
| 5,503,157 A | 4/1996 | Sramek |
| 5,505,209 A | 4/1996 | Reining |
| 5,511,553 A | 4/1996 | Segalowitz |
| 5,529,072 A | 6/1996 | Sramek |
| 5,544,662 A | 8/1996 | Saulnier et al. |
| 5,557,242 A | 9/1996 | Wetherell |
| 5,562,607 A | 10/1996 | Gyory |
| 5,588,429 A | 12/1996 | Isaacson et al. |
| 5,704,355 A | 1/1998 | Bridges |
| 5,730,136 A | 3/1998 | Laufer et al. |
| 5,732,710 A | 3/1998 | Rabinovich et al. |
| 5,746,214 A | 5/1998 | Brown et al. |
| 5,759,159 A | 6/1998 | Masreliez |
| 5,788,643 A | 8/1998 | Feldman |
| 5,800,350 A | 9/1998 | Coppleson et al. |
| 5,807,251 A | 9/1998 | Wang et al. |
| 5,807,270 A | 9/1998 | Williams |
| 5,807,272 A | 9/1998 | Kun et al. |
| 5,810,742 A | 9/1998 | Pearlman |
| 5,919,142 A | 7/1999 | Boone et al. |
| 5,994,956 A * | 11/1999 | Concorso ............ 330/107 |
| 6,006,125 A | 12/1999 | Kelly et al. |
| 6,011,992 A | 1/2000 | Hubbard et al. |
| 6,015,389 A | 1/2000 | Brown |
| 6,018,677 A | 1/2000 | Vidrine et al. |
| 6,122,544 A | 9/2000 | Organ |
| 6,125,297 A | 9/2000 | Siconolfi |
| 6,142,949 A | 11/2000 | Ubby |
| 6,151,523 A | 11/2000 | Ferrer et al. |
| 6,173,003 B1 | 1/2001 | Whikehart et al. |
| 6,228,022 B1 | 5/2001 | Friesem et al. |
| 6,228,033 B1 | 5/2001 | Koobi |
| 6,233,473 B1 | 5/2001 | Shepherd et al. |
| 6,236,886 B1 | 5/2001 | Cherepenin et al. |
| 6,248,083 B1 | 6/2001 | Smith et al. |
| 6,256,532 B1 | 7/2001 | Cha |
| 6,292,690 B1 | 9/2001 | Petrucelli et al. |
| 6,339,722 B1 | 1/2002 | Heethaar et al. |
| 6,354,996 B1 | 3/2002 | Drinan et al. |
| 6,496,725 B2 | 12/2002 | Kamada et al. |
| 6,497,659 B1 | 12/2002 | Rafert |
| 6,532,384 B1 | 3/2003 | Fukuda |
| 6,560,480 B1 | 5/2003 | Nachaliel et al. |
| 6,569,160 B1 | 5/2003 | Goldin et al. |
| 6,584,348 B2 | 6/2003 | Glukhovsky |
| 6,618,616 B2 | 9/2003 | Iijima et al. |
| 6,623,312 B2 | 9/2003 | Merry et al. |
| 6,625,487 B2 | 9/2003 | Herleikson |
| 6,631,292 B1 | 10/2003 | Liedtke |
| 6,633,777 B2 | 10/2003 | Szopinski |
| 6,643,543 B2 | 11/2003 | Takehara et al. |
| 6,714,813 B2 | 3/2004 | Ishigooka et al. |
| 6,714,814 B2 | 3/2004 | Yamada et al. |
| 6,723,049 B2 | 4/2004 | Skladnev et al. |
| 6,724,200 B2 | 4/2004 | Fukuda |
| 6,760,617 B2 | 7/2004 | Ward et al. |
| 6,768,921 B2 | 7/2004 | Organ et al. |
| 6,845,264 B1 | 1/2005 | Skladnev et al. |
| 6,870,109 B1 | 3/2005 | Villarreal |
| 6,906,533 B1 | 6/2005 | Yoshida |
| 6,922,586 B2 | 7/2005 | Davies |
| 6,980,853 B2 | 12/2005 | Miyoshi et al. |
| 7,130,680 B2 * | 10/2006 | Kodama et al. ............ 600/547 |
| 7,132,611 B2 | 11/2006 | Gregaard et al. |
| 7,148,701 B2 | 12/2006 | Park et al. |
| 7,212,852 B2 | 5/2007 | Smith et al. |
| 7,457,660 B2 | 11/2008 | Smith et al. |
| 7,477,937 B2 | 1/2009 | Iijima et al. |
| 7,706,872 B2 | 4/2010 | Min et al. |
| 7,733,224 B2 | 6/2010 | Tran |
| 7,749,013 B2 | 7/2010 | Sato et al. |
| 8,233,974 B2 * | 7/2012 | Ward et al. ............ 600/547 |
| 2001/0007056 A1 | 7/2001 | Linder et al. |
| 2001/0007924 A1 | 7/2001 | Kamada et al. |
| 2001/0020138 A1 | 9/2001 | Ishigooka et al. |
| 2001/0025139 A1 | 9/2001 | Pearlman |
| 2002/0072686 A1 | 1/2002 | Hoey et al. |
| 2002/0020138 A1 | 2/2002 | Walker et al. |
| 2002/0022787 A1 | 2/2002 | Takehara et al. |
| 2002/0079910 A1 | 6/2002 | Fukuda |
| 2002/0093992 A1 | 7/2002 | Plangger |
| 2002/0109621 A1 | 8/2002 | Khair et al. |
| 2002/0123694 A1 | 9/2002 | Organ et al. |
| 2002/0161311 A1 | 10/2002 | Ward et al. |
| 2002/0193689 A1 | 12/2002 | Bernstein et al. |
| 2002/0194419 A1 | 12/2002 | Rajput et al. |
| 2003/0004403 A1 | 1/2003 | Drinan et al. |
| 2003/0023184 A1 | 1/2003 | Pitts-Crick et al. |
| 2003/0028221 A1 | 2/2003 | Zhu et al. |
| 2003/0050570 A1 | 3/2003 | Kodama et al. |
| 2003/0073916 A1 | 4/2003 | Yonce |
| 2003/0105411 A1 | 6/2003 | Smallwood et al. |
| 2003/0120170 A1 | 6/2003 | Zhu et al. |
| 2004/0015095 A1 | 1/2004 | Li et al. |
| 2004/0019292 A1 | 1/2004 | Drinan et al. |
| 2004/0059242 A1 | 3/2004 | Masuo et al. |
| 2004/0077944 A1 | 4/2004 | Steinberg et al. |
| 2004/0158167 A1 | 8/2004 | Smith et al. |
| 2004/0167423 A1 | 8/2004 | Pillon et al. |
| 2004/0181164 A1 | 9/2004 | Smith et al. |
| 2004/0186392 A1 | 9/2004 | Ward et al. |
| 2004/0210150 A1 | 10/2004 | Virtanen |
| 2004/0210158 A1 | 10/2004 | Organ et al. |
| 2004/0252870 A1 | 12/2004 | Reeves et al. |
| 2004/0253652 A1 | 12/2004 | Davies |

(56) References Cited

U.S. PATENT DOCUMENTS

| | | |
|---|---|---|
| 2004/0267344 A1 | 12/2004 | Stett et al. |
| 2005/0039763 A1 | 2/2005 | Kraemer et al. |
| 2005/0049474 A1 | 3/2005 | Kellogg et al. |
| 2005/0098343 A1 | 5/2005 | Fukuda |
| 2005/0101875 A1 | 5/2005 | Semler et al. |
| 2005/0107719 A1 | 5/2005 | Arad et al. |
| 2005/0113704 A1 | 5/2005 | Lawson et al. |
| 2005/0124908 A1 | 6/2005 | Belalcazar et al. |
| 2005/0137480 A1 | 6/2005 | Alt et al. |
| 2005/0151545 A1 | 7/2005 | Park et al. |
| 2005/0177062 A1 | 8/2005 | Skrabal et al. |
| 2005/0192488 A1 | 9/2005 | Bryenton et al. |
| 2005/0203435 A1 | 9/2005 | Nakada |
| 2005/0261743 A1 | 11/2005 | Kroll |
| 2006/0004300 A1 | 1/2006 | Kennedy |
| 2006/0085048 A1 | 4/2006 | Cory et al. |
| 2006/0085049 A1 | 4/2006 | Cory et al. |
| 2006/0111652 A1 | 5/2006 | McLeod |
| 2006/0116599 A1 | 6/2006 | Davis |
| 2006/0122523 A1 | 6/2006 | Bonmassar et al. |
| 2006/0122540 A1 | 6/2006 | Zhu et al. |
| 2006/0197509 A1 | 9/2006 | Kanamori et al. |
| 2006/0224079 A1 | 10/2006 | Washchuk |
| 2006/0224080 A1 | 10/2006 | Oku et al. |
| 2006/0264775 A1 | 11/2006 | Mills et al. |
| 2006/0270942 A1 | 11/2006 | McAdams |
| 2007/0010758 A1 | 1/2007 | Matthiessen et al. |
| 2007/0027402 A1 | 2/2007 | Levin et al. |
| 2007/0043303 A1 | 2/2007 | Osypka et al. |
| 2007/0087703 A1 | 4/2007 | Li et al. |
| 2007/0106342 A1 | 5/2007 | Schumann |
| 2008/0002873 A1 | 1/2008 | Reeves et al. |
| 2008/0004904 A1 | 1/2008 | Tran |
| 2008/0009757 A1 | 1/2008 | Tsoglin et al. |
| 2008/0009759 A1* | 1/2008 | Chetham ................... 600/526 |
| 2008/0039700 A1 | 2/2008 | Drinan et al. |
| 2008/0091114 A1 | 4/2008 | Min et al. |
| 2008/0188757 A1 | 8/2008 | Rovira et al. |
| 2008/0205717 A1 | 8/2008 | Reeves et al. |
| 2008/0319336 A1 | 12/2008 | Ward et al. |
| 2009/0043222 A1 | 2/2009 | Chetham |
| 2009/0054952 A1 | 2/2009 | Glukhovsky et al. |
| 2009/0076343 A1 | 3/2009 | James et al. |
| 2009/0076345 A1 | 3/2009 | Manicka et al. |
| 2009/0076350 A1 | 3/2009 | Bly et al. |
| 2009/0082679 A1 | 3/2009 | Chetham |
| 2009/0105555 A1 | 4/2009 | Dacso et al. |
| 2009/0143663 A1 | 6/2009 | Chetham |
| 2009/0177099 A1 | 7/2009 | Smith et al. |
| 2009/0287102 A1 | 11/2009 | Ward |
| 2009/0318778 A1 | 12/2009 | Dacso et al. |
| 2010/0168530 A1 | 7/2010 | Chetham et al. |
| 2011/0060239 A1 | 3/2011 | Gaw |
| 2011/0118619 A1 | 5/2011 | Burton et al. |

FOREIGN PATENT DOCUMENTS

| | | |
|---|---|---|
| CA | 2613524 | 1/2007 |
| CA | 2615845 | 1/2007 |
| DE | 2912349 | 10/1980 |
| EP | 0249823 | 12/1987 |
| EP | 349043 | 3/1990 |
| EP | 0357309 | 3/1990 |
| EP | 377887 | 7/1990 |
| EP | 339471 | 3/1997 |
| EP | 865763 | 9/1998 |
| EP | 0869360 | 10/1998 |
| EP | 1112715 | 4/2001 |
| EP | 1146344 | 10/2001 |
| EP | 1114610 | 11/2001 |
| EP | 1177760 | 2/2002 |
| EP | 1219937 | 7/2002 |
| EP | 1238630 | 9/2002 |
| EP | 1338246 | 8/2003 |
| EP | 1452131 | 9/2004 |
| EP | 1553871 | 7/2005 |
| EP | 1629772 | 3/2006 |
| EP | 1247487 | 1/2008 |
| EP | 1903938 | 4/2008 |
| EP | 1909642 | 4/2008 |
| EP | 1948017 | 7/2008 |
| FR | 2486386 | 1/1982 |
| FR | 2748928 | 11/1997 |
| GB | 2131558 | 6/1984 |
| GB | 2260416 | 4/1993 |
| GB | 2426824 | 12/2006 |
| JP | 8191808 | 7/1996 |
| JP | 09051884 | 2/1997 |
| JP | 9220209 | 8/1997 |
| JP | 10000185 | 1/1998 |
| JP | 10014898 | 1/1998 |
| JP | 10014899 | 2/1998 |
| JP | 11070090 | 3/1999 |
| JP | 2000107138 | 4/2000 |
| JP | 2000139867 | 5/2000 |
| JP | 2001224568 | 8/2001 |
| JP | 2001321352 | 11/2001 |
| JP | 2002330938 | 11/2002 |
| JP | 2003116805 | 4/2003 |
| JP | 2003230547 | 8/2003 |
| JP | 200461251 | 2/2004 |
| JP | 2008022995 | 7/2008 |
| RU | 2112416 | 6/1998 |
| WO | WO 93-18821 | 9/1993 |
| WO | WO 96-01586 | 1/1996 |
| WO | WO 96-12439 | 5/1996 |
| WO | WO 96-32652 | 10/1996 |
| WO | WO 97-11638 | 4/1997 |
| WO | WO 97-14358 | 4/1997 |
| WO | WO 98-06328 | 2/1998 |
| WO | WO 98-23204 | 6/1998 |
| WO | WO 98-33553 | 8/1998 |
| WO | WO 88-07392 | 10/1998 |
| WO | WO 00-40955 | 7/2000 |
| WO | WO 00-79255 | 12/2000 |
| WO | WO 01-50954 | 7/2001 |
| WO | WO 01-67098 | 9/2001 |
| WO | WO 02-53028 | 7/2002 |
| WO | WO 02-62214 | 8/2002 |
| WO | WO 04-00115 | 12/2003 |
| WO | WO 04-26136 | 4/2004 |
| WO | WO 04-32738 | 4/2004 |
| WO | WO 2004-043252 | 5/2004 |
| WO | WO 2004-047635 | 6/2004 |
| WO | WO 2004-047636 | 6/2004 |
| WO | WO 2004-047638 | 6/2004 |
| WO | WO 2004-083804 | 9/2004 |
| WO | WO 2004-098389 | 11/2004 |
| WO | WO 2005-018432 | 3/2005 |
| WO | WO 2005-027717 | 3/2005 |
| WO | WO 2005-051194 | 6/2005 |
| WO | WO 2005-122888 | 12/2005 |
| WO | WO 2006-129108 | 12/2006 |
| WO | WO 2006-129116 | 12/2006 |
| WO | WO 2007-002991 | 1/2007 |
| WO | WO 2007-002992 A1 * | 1/2007 |
| WO | WO 2007-009183 | 1/2007 |
| WO | WO 2007-041783 | 4/2007 |
| WO | WO 2007-056493 | 5/2007 |
| WO | WO 2007-105996 | 9/2007 |
| WO | WO 2008-054426 | 8/2008 |
| WO | WO 2008-138062 | 11/2008 |
| WO | WO 2009-036369 | 3/2009 |
| WO | WO 2009-100491 | 8/2009 |
| WO | WO 2011-022068 | 2/2011 |
| WO | WO 2011-050393 | 5/2011 |
| WO | WO 2011-075769 | 6/2011 |

OTHER PUBLICATIONS

Abdullah M. Z.; Simulation of an inverse problem in electrical impedance tomography using resistance electrical network analogues; International Journal of Electrical Engineering Education; vol. 36, No. 4, pp. 311-324; Oct. 1999.

(56) References Cited

OTHER PUBLICATIONS

Al-Hatib, F.; Patient Instrument connection errors in bioelectrical impedance measurement; Physiological Measurement; vol. 19, No. 2, pp. 285-296; May 2, 1998.
Bella, et al., Relations of Left Ventricular Mass to Fat-Free and Adipose Body Mass: The Strong Heart Study, (1998) Circulation, vol. 98, pp. 2538-2544.
Boulier, A. et al.; Fat-Free Mass Estimation by Two Electrode Impedance Method; American Journal of Clinical Nutrition; vol. 52, pp. 581-585; 1990.
Bracco, D. et al., Bedside determination of fluid accumulation after cardiac surgery using segmental bioelectrical impedance, Critical Care Medicine, vol. 26, No. 6, pp. 1065-1070, 1998.
Chaudary, S.S. et al.; Dielectric Properties of Normal & Malignant Human Breast Tissues at Radiowave and Microwave Frequencies; Indian Journal of Biochemistry & Biophysics; vol. 21, No. 1, pp. 76-79; 1984.
Chiolero, R.L. et al.; Assessment of changes in body water by bioimpedance in acutely ill surgical patients; Intensive Care Medicine; vol. 18, pp. 322-326; 1992.
Chumlea et al.; Bioelectrical Impedance and Body Composition: Present Status and Future Directions; Nutrition Reviews; vol. 52, No. 4, pp. 123-131; 1994.
Cornish, B.H. et al.; Alteration of the extracellular and total body water volumes measured by multiple frequency bioelectrical impedance analysis; Nutrition Research; vol. 14, No. 5, pp. 717-727; 1994.
Cornish, B.H. et al.; Bioelectrical impedance for monitoring the efficacy of lymphoedema treatment programmes; Breast Cancer Research and Treatment; vol. 38, pp. 169-176; 1996.
Cornish, B.H. et al.; Data analysis in multiple-frequency bioelectrical impedance analysis; Physiological Measurement; vol. 19, No. 2, pp. 275-283; May 1, 1998.
Cornish, B.H. et al.; Early diagnosis of lymphedema using multiple frequency bioimpedance; Lymphology; vol. 34, pp. 2-11; Mar. 2001.
Cornish, B.H. et al.; Early diagnosis of lymphoedema in postsurgery breast cancer patients; Annals New York Academy of Sciences; pp. 571-575; May 2000.
Cornish, B.H. et al.; Quantification of Lymphoedema using Multi-frequency Bioimpedance; Applied Radiation and Isotopes; vol. 49, No. 5/6, pp. 651-652; 1998.
De Luca, F. et al., Use of low-frequency electrical impedance measurements to determine phospoholipid content in amniotic fluid; Physics in Medicine and Biology, vol. 41, pp. 1863-1869, 1996.
Deurenberg, P. et al., Multi-frequency bioelectrical impedance: a comparison between the Cole-Cole modelling and Hanai equations with the classically impedance index approach, Annals of Human Biology, vol. 23, No. 1, pp. 31-40, 1996.
Dines K.A. et al.; Analysis of electrical conductivity imaging; Geophysics; vol. 46, No. 7, pp. 1025-1036; Jul. 1981.
Ellis, K.J. et al; Human hydrometry: comparison of multifrequency bioelectrical impedance with 2H2O and bromine dilution; Journal of Applied Physiology; vol. 85, No. 3, pp. 1056-1062; 1998.
Forslund, A.H. et al.; Evaluation of modified multicompartment models to calculate body composition in healthy males; American Journal of Clinical Nutrition; vol. 63, pp. 856-62; 1996.
Gersing, E.; Impedance spectroscopy on living tissue for determination of the state of Organs; Bioelectrochemistry and Bioenergetics; vol. 45, pp. 145-149; 1998.
Gerth, W.A. et al.; A computer-based bioelectrical impedance spectroscopic system for noninvasive assessment of compartmental fluid redistribution; Third Annual IEEE Symposium on Computer Based Medical Systems, Jun. 3-6, 1990, University of NC. At Chapel Hill; pp. 446-453; Jun. 1990.
Gudivaka R. et al; Single—and multifrequency models for bioelectrical impedance analysis of body water compartments; Applied Physiology; vol. 87, Issue 3, pp. 1087-1096; 1999.
Iacobellis, G., et al. Influence of Excess Fat on Cardiac Morphology and Function: Study in Uncomplicated Obesity, (2002) Obesity Research, vol. 10, pp. 767-773.

Jones, C.H. et al; Extracellular fluid volume determined by bioelectric impedance and serum albumin in CAPD patients; Nephrology Dialysis Transplantation; vol. 13, pp. 393-397; 1998.
Jossinet, J. et al.; A Study for Breast Imaging with a Circular Array of Impedance Electrodes; Proc. Vth Int. Conf. Bioelectrical Impedance, 1981, Tokyo, Japan; pp. 83-86; 1981.
Jossinet, J. et al.; Technical Implementation and Evaluation of a Bioelectrical Breast Scanner; Proc. 10.sup.th Int. Conf. IEEE Engng. Med. Biol., 1988, New Orleans, USA (Imped. Imaging II); vol. 1. p. 289; 1988.
Kanai, H. et al.; Electrical Measurement of Fluid Distribution in Legs and Arms; Medical Progress through technology; pp. 159-170; 1987.
Karason, K., et al., Impact of Blood Pressure and Insulin on the Relationship Between Body Fat and Left Ventricular Structure, (2003) European Heart Journal, vol. 24, pp. 1500-1505.
Kim, C.T. et al.; Bioelectrical impedance changes in regional extracellular fluid alterations; Electromyography and Clinical Neurophysiology; vol. 37, pp. 297-304; 1997.
Liu R. et al; Primary Multi-frequency Data Analyze in Electrical Impedance Scanning; Proceedings of the IEEE-EMBS 2005, 27th Annual International Conference of the Engineering in Medicine and Biology Society, Shanghai, China; pp. 1504-1507; , Sep. 1-4, 2005.
Lozano, A. et al.; Two-frequency impedance plethysmograph: real and imaginary parts; Medical & Biological Engineering & Computing; vol. 28, No. 1, pp. 38-42; Jan. 1990.
Lukaski, H.C. et al.; Estimation of Body Fluid volumes Using Tetrapolar Bioelectrical Impedance Measurements; Aviation, Space, and Environmental Medicine; pp. 1163-1169; Dec. 1988.
Man, B. et al. Results of Preclinical Tests for Breast Cancer Detection by Dielectric Measurements; XII Int. Conf. Med. Biol. Engng. 1979, Jerusalem, Israel. Springer Int., Berlin; Section 30.4; 1980.
Mattar, J.A., Application of Total Body Impedance to the Critically Ill Patient, New Horizons, vol. 4, No. 4, pp. 493-503, Nov. 1996.
McCullagh, W. A. et al., IFMBE Proceedings, vol. 17, p. 619, 2007.
McDougal D., et al.; Body Composition Measurements From Whole Body Resistance and Reactance; Surgical Forum; vol. 36, pp. 43-44; 1986.
Osterman K.S. et al.; Multifrequency electrical impedance imaging: preliminary in vivo experience in breast; Physiological Measurement; vol. 21, No. 1, pp. 99-109; Feb. 2000.
Ott, M. et al.; Bioelectrical Impedance Analysis as a Predictor of Survival in Patients with Human Immunodeficiency Virus Infection; Journal of Acquired Immune Deficiency Syndromes and Human Retrovirology; vol. 9, pp. 20-25; 1995.
Pethig, R. et al.; The Passive Electrical Properties of Biological Systems: Their Significance in Physiology, Biophysics and Biotechnology; Physics in Medicine and Biology; vol. 32, pp. 933-970; 1987.
Piperno, G. et al.; Breast Cancer Screening by Impedance Measurements; Frontiers of Medical & Biological Engineering; vol. 2, pp. 111-117; 1990.
Rigaud, B. et al.; Bioelectrical Impedance Techniques in Medicine; Critical Reviews in Biomedical Engineering; vol. 24 (4-6), pp. 257-351; 1996.
Schneider, I.; Broadband signals for electrical impedance measurements for long bone fractures; Engineering in Medicine and Biology Society, 1996. Bridging Disciplines for Biomedicine. Proceedings of the 18th Annual International Conference of the IEEE; vol. 5, pp. 1934-1935; Oct. 31, 1996.
Skidmore, R. et al.; A Data Collection System for Gathering Electrical Impedance Measurements from the Human Breast; Clinical Physics Physiological Measurement; vol. 8, pp. 99-102; 1987.
Sollish, B.D. et al.; Microprocessor-assisted Screening Techniques; Israel Journal of Medical Sciences; vol. 17, pp. 859-864; 1981.
Steijaert, M. et al.; The use of multi-frequency impedance to determine total body water and extracellular water in obese and lean female individuals; International Journal of Obesity; vol. 21, pp. 930-934; 1997.
Surowiec, A.J. et al.; Dielectric Properties of Brest Carcinoma and the Surrounding Tissues; IEEE Transactions on Biomedical Engineering; vol. 35, pp. 257-263; 1988.

(56) References Cited

OTHER PUBLICATIONS

Tedner, B.; Equipment Using Impedance Technique for Automatic Recording of Fluid-Volume Changes During Haemodialysis; Medical & Biological Engineering & Computing; pp. 285-290; 1983.

Thomas. B.J. et al.; Bioelectrical impedance analysis for measurement of body fluid volumes—A review; Journal of Clinical Engineering; vol. 17, No. 16, pp. 505-510; 1992.

Thomas. B.J. et al.; Bioimpedance Spectrometry in Determination of Body Water Compartments: Accuracy and Clinical Significance; Applied Radiation and Isotopes; vol. 49, No. 5/6, pp. 447-455; 1998.

Thomas. B.J.; Future Technologies; Asia Pacific Journal Clinical Nutrition; vol. 4, pp. 157-159; 1995.

Ulgen, Y. et al.; Electrical parameters of human blood; Engineering in Medicine and Biology Society, 1998. Proceedings of the 20th Annual International Conference of the IEEE; vol. 6, pp. 2983-2986; Nov. 1, 1998.

Ward, L.C. et al., Multi-frequency bioelectrical impedance augments the diagnosis and management of lymphoedema in post-mastectomy patients, European Journal of Clinical Investigation, vol. 22, pp. 751-754, 1992.

Ward, L.C. et al.; Determination of Cole parameters in multiple frequency bioelectrical impedance analysis using only the measurement of impedances; Four-frequency fitting; Physiological Measurement; vol. 27, No. 9, pp. 839-850; Sep. 2006.

Ward, L.C. et al.; There is a better way to measure Lymphoedema; National Lymphedema Network Newsletter; vol. 7, No. 4, pp. 89-92; Oct. 1995.

Woodrow, G. et al; Effects of icodextrin in automated peritoneal dialysis on blood pressure and bioelectrical impedance analysis; Nephrology Dialysis Transplantation; vol. 15, pp. 862-866; 2000.

Yoshinaga, M., Effect of Total Adipose Weight and Systemic Hypertension on Left Ventricular Mass in Children, American Journal of Cardiology, (1995) vol. 76, pp. 785-787.

International Search Report and Written Opinion of the International Searching Authority issued in PCT/AU2009/000163 dated Apr. 16, 2009.

International Search Report and Written Opinion of the International Searching Authority issued in PCT/AU2006/000922 dated Oct. 10, 2006.

International Search Report and Written Opinion of the International Searching Authority issued in PCT/AU2006/001057 dated Oct. 25, 2006.

International Search Report and Written Opinion of the International Searching Authority issued in PCT/AU2008/000034 dated Mar. 17, 2008.

International Search Report and Written Opinion of the International Searching Authority issued in PCT/AU2008/000588 dated Aug. 13, 2008.

* cited by examiner

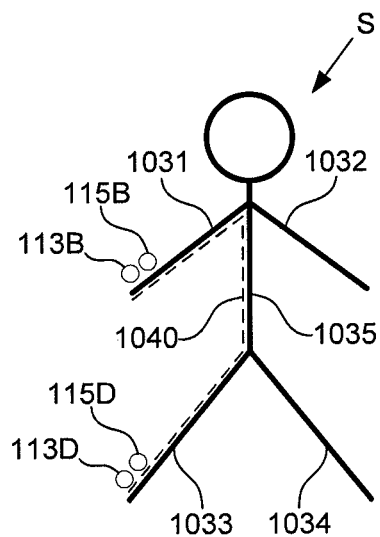
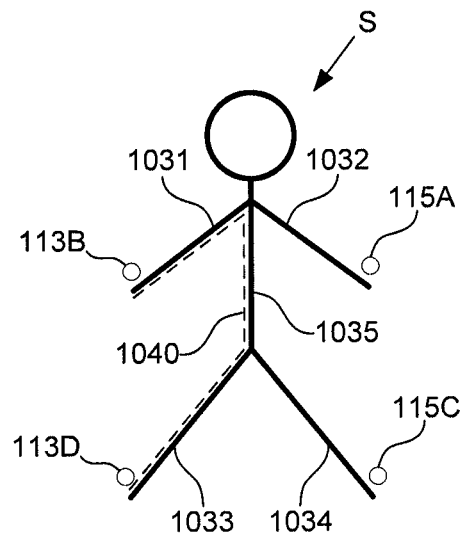
Fig. 10A  Fig. 10B
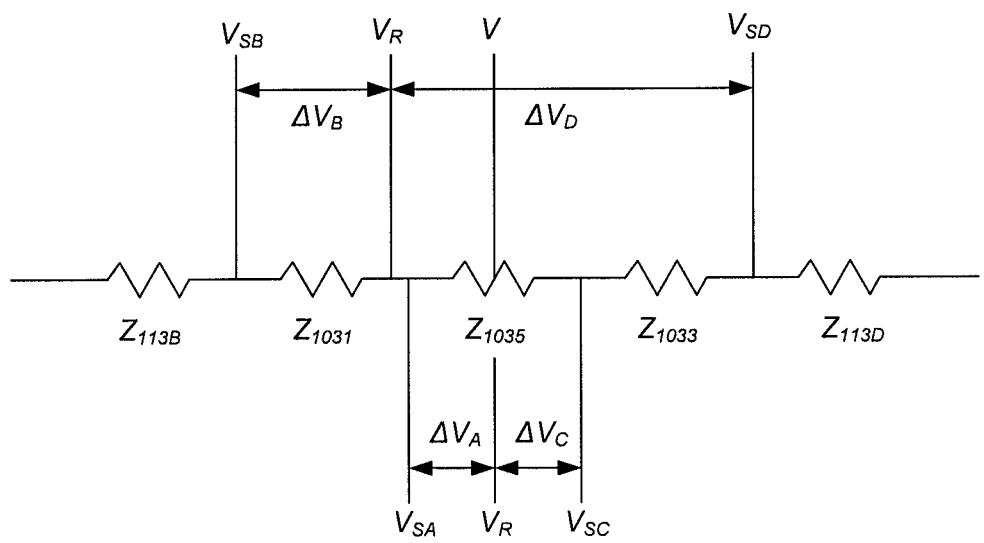
Fig. 10C

IMPEDANCE DETERMINATION

RELATED APPLICATIONS

This application is a U.S. National Phase under 35 U.S.C. §371 of International Patent Application No. PCT/AU2008/001521, filed Oct. 15, 2008, which claims the benefit of Australian Application No. 2007906049, filed Nov. 5, 2007.

BACKGROUND OF THE INVENTION

The present invention relates to a method and apparatus for use in performing impedance measurements on a subject.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

One existing technique for determining biological indicators relating to a subject, such as cardiac function, body composition, and other health status indicators, such as the presence of oedema, involves the use of bioelectrical impedance. This process typically involves using a measuring device to measure the electrical impedance of a subject's body using a series of electrodes placed on the skin surface. Changes in electrical impedance measured at the body's surface are used to determine parameters, such as changes in fluid levels, associated with the cardiac cycle, oedema, or the like.

Impedance measuring apparatus is sometimes sensitive to external factors, including stray capacitances between the subject and the local environment and the measurement apparatus, variations in electrode/tissue interface impedances, also known as electrode impedances, as well as stray capacitances and inductive coupling between the leads used to connect the measuring device to the electrodes.

SUMMARY OF THE PRESENT INVENTION

The present invention seeks to substantially overcome, or at least ameliorate, one or more disadvantages of existing arrangements.

In a first broad form the present invention seeks to provides apparatus for use in performing impedance measurements on a subject, wherein the apparatus includes a processing system for:
  a) causing a first signal to be applied to the subject;
  b) determining an indication of a second signal measured across the subject;
  c) using the indication of the second signal to determine if an unacceptable imbalance exists; and,
  d) if an unacceptable imbalance exists:
     i) determining a modified first signal in accordance with the imbalance; and,
     ii) causing the modified first signal to be applied to the subject to thereby allow at least one impedance measurement to be performed.

Typically the processing system is for:
  a) comparing the second signal to a threshold; and,
  b) determining if an unacceptable imbalance exists depending on the results of the comparison.

Typically the second signal includes voltages sensed at respective second electrodes, and wherein the processing system is for:
  a) determining the voltage sensed at each of the second electrodes;
  b) determining an additive voltage; and,
  c) determining the imbalance using the additive voltage.

Typically the additive voltage is a common mode signal.

Typically the processing system is for determining the modified first signal so as to reduce the imbalance.

Typically first signals are applied to the subject via at least two first electrodes, and wherein the processing system is for modifying the first signal by modifying at least one of a phase and a magnitude of at least one first signal applied to at least one of the first electrodes.

Typically:
  a) the first signal is applied via first electrodes coupled to first and second limbs of the subject; and,
  b) the second signal is sensed via second electrodes coupled to third and fourth limbs of the subject, the third and fourth limbs being different to the first and second limbs.

Typically the processing system is for:
  a) causing the first signal to be applied via first electrodes;
  b) determining indications of second signals sensed at each of a number of second electrodes;
  c) selecting second signals sensed at selected ones of the second electrodes; and,
  d) determining any imbalance using the selected second signals.

Typically the first signal includes voltages applied to the subject using first electrodes and the second signal includes voltages sensed at respective second electrodes.

Typically the processing system is for performing an impedance measurement by:
  a) determining a sensed current caused by applying the first signal to the subject;
  b) determining a sensed voltage across the subject; and,
  c) determining an impedance parameter using the sensed current and voltage.

Typically the processing system is for:
  a) determining a sensed current caused by applying the first signal to the subject;
  b) comparing the sensed current to a threshold; and,
  c) selectively halting the impedance measurement process depending on the results of the comparison.

Typically the processing system is for:
  a) determining a sensed current caused by applying the first signal to the subject; and,
  b) using the sensed current in determining the modified first signal.

Typically the processing system is for:
  a) causing a first signal to be applied to the subject at a first frequency;
  b) determining an indication of a second signal measured across the subject;
  c) using the indication of the second signal to determine any imbalance;
  d) if no unacceptable imbalance exists, using at least the indication of the second signal to determine at least one impedance value;
  e) if an unacceptable imbalance exists:
     i) determining a modified first signal in accordance with the imbalance;
     ii) causing the modified first signal to be applied to the subject;

iii) determining an indication of a modified second signal measured across the subject; and
iv) repeating steps c) to e) for the indication of the modified second signal;

f) repeating steps a) to e) for at least one second frequency.

Typically the processing system is for:
a) causing voltage drive signals to be applied to the subject via first electrodes;
b) determining sensed current signals caused by the voltage drive signals;
c) determining sensed voltages measured via respective second electrodes;
d) determining a body centre voltage from the sensed voltages;
e) determining upper and lower impedances for the subject using the sensed current signals, the voltage drive signals and the body centre voltage; and,
f) determining modified voltage drive signals using the upper and lower impedances and an ideal current signal indication.

Typically the voltage drive signals include first and second voltage drive signals applied to the subject via respective first electrodes, the first voltage drive signal having a first magnitude and first phase, and the second voltage drive signal having a second magnitude and second phase and wherein the processing system is for determining the modified voltage drive signals by modifying at least one of:
a) the first phase;
b) the first magnitude;
c) the second phase; and,
d) the second magnitude.

Typically the processing system is for:
a) causing the modified voltage drive signals to be applied to the subject;
b) determining sensed voltages measured via respective second electrodes;
c) determining if an unacceptable imbalance exists using the sensed voltages; and,
d) if an unacceptable imbalance exists:
   i) determining further modified voltage drive signals; and,
   ii) repeating steps (a) to (d) until any imbalance is acceptable.

Typically the method includes performing impedance measurements at multiple frequencies, in turn.

Typically the method includes:
a) for a first frequency:
   i) determining a modified first signal that results in an acceptable imbalance; and,
   ii) causing an impedance measurement to be performed using the modified first signal; and,
b) for a second frequency:
   i) causing a first signal to be applied to the subject, the first signal being based on the modified first signal determined for the first frequency; and,
   ii) determining if an unacceptable imbalance exists.

Typically the method includes:
a) for a first frequency:
   i) causing first and second voltage drive signals to be applied to the subject via respective first electrodes;
   ii) determining modified first and second voltage drive signals that result in an acceptable imbalance, the first voltage drive signal having a first magnitude and first phase, and the second voltage drive signal having a second magnitude and second phase; and,
b) for a second frequency:
   i) causing first and second voltage drive signals to be applied to the subject, the first voltage drive signal having the first magnitude and the first phase, and the second voltage drive signal having the second magnitude and the second phase; and,
   ii) determining if an unacceptable imbalance exists.

Typically the processing system is for:
a) generating control signals;
b) transferring the control signals to at least one signal generator thereby causing the first signal to be applied to the subject;
c) receiving an indication of the one or more signals applied to the subject from the at least one signal generator;
d) receiving an indication of one or more second signals measured across the subject from at least one sensor; and,
e) performing at least preliminary processing of the indications to thereby allow impedance values to be determined.

Typically the apparatus includes a differential amplifier for amplifying second signals measured at each of two second electrodes.

Typically the differential amplifier generates at least one of:
a) a differential voltage indicative of the voltage measured at the second electrodes; and,
b) a common mode signal indicative of any imbalance.

Typically the apparatus includes at least one signal generator for applying the first signal to the subject via a first electrode.

Typically each signal generator is for:
a) receiving one or more control signals from the processing system; and,
b) amplifying the control signals to thereby generate the first signal.

Typically each signal generator is for:
a) determining a sensed current caused by applying the first signal to the subject; and,
b) providing an indication of the sensed current to the processing system.

Typically the apparatus includes at least two signal generators, each signal generator being for connection to a respective first electrode.

Typically the apparatus includes at least one sensor for measuring the second signal via second electrodes.

Typically the apparatus includes at least two sensors, each sensor being for connection to a respective second electrode.

Typically the apparatus includes a number of electrode systems, and wherein each electrode system includes:
a) a sensor; and,
b) a signal generator.

Typically electrode system includes:
a) a first substrate having the signal generator and sensor mounted thereon; and,
b) a second substrate having at least two conductive pads mounted thereon, the conductive pads forming a first and a second electrode for coupling the signal generator and the sensor to a subject in use.

Typically the electrode system includes a capacitive cancelling circuit for cancelling capacitive coupling between the first and second electrodes.

Typically the capacitive cancelling circuit includes an inverting amplifier for coupling a signal generator output to a sensor input.

Typically the inverting amplifier applies a capacitive cancelling signal to the sensor input to thereby cancel any effective capacitance between the first electrode and the second electrode.

Typically an inverting amplifier output is coupled to the sensor input via at least one of:
 a) a resistor;
 b) a capacitor; and,
 c) an inductor.

Typically at least one of a resistor and capacitor are adjustable, thereby allowing a capacitive cancelling signal applied to the sensor input to be controlled.

Typically the electrode system includes an input capacitance cancelling circuit for cancelling an effective input capacitance at a sensor input.

Typically the electrode system includes a feedback loop for connecting a sensor output to the sensor input.

Typically the feedback loop includes at least one of:
 a) a resistor;
 b) a capacitor; and,
 c) an inductor.

Typically at least one of a resistor and capacitor are adjustable, thereby allowing a current flow from the sensor output to the sensor input to be controlled.

Typically the feedback loop applies an input capacitance cancelling signal to the sensor input to thereby cancel any effective capacitance at the sensor input.

Typically the apparatus includes:
 a) a number of electrode systems, and wherein each electrode system includes a signal generator and sensor; and,
 b) at number of leads for connecting the measuring device to the electrode systems, each lead including:
  i) at least two connections for connecting the measuring device and the signal generator, and the measuring device and the sensor; and,
  ii) a shield for each of the at least two connections, the shields being electrically connected, and connected to a reference voltage in each of the measuring device and the electrode system.

Typically the apparatus includes:
 a) at least two electrode systems, each electrode system including:
  i) a signal generator for applying a first signal to the subject;
  ii) a sensor for sensing a second signal across the subject;
  iii) a first electrode for coupling the signal generator to the subject; and,
  iv) a second electrode for coupling the sensor to the subject; and,
 b) a measuring device for controlling the electrode systems to allow impedance measurements to be performed; and,
 c) at least two leads for connecting the measuring device to the electrode systems.

Typically the leads are arranged in use to at least one of:
 i) extend from the measuring device in different directions to thereby reduce inductive coupling therebetween; and,
 ii) minimise the lead length.

Typically the apparatus includes an interface for coupling the processing system to a computer system, the processing system being for:
 a) generating control signals in accordance with commands received from the computer system; and,
 b) providing data indicative of measured impedance values to the computer system to allow impedance values to be determined.

Typically the first signal is includes two first signals applied to the subject via at least two first electrodes, and the second signal includes two second signals sensed at two second electrodes.

In a second broad form the present invention seeks to provides apparatus for use in performing impedance measurements on a subject, wherein the apparatus includes a number of electrode systems, and wherein each electrode system includes:
 a) a first substrate having a signal generator and sensor mounted thereon, the signal generator being for applying a first signal to the subject and the sensor for sensing a second signal across the subject; and,
 b) a second substrate having at least two conductive pads mounted thereon, the conductive pads forming first and second electrodes for coupling the signal generator and the sensor to a subject in use.

Typically the electrode system includes a capacitive cancelling circuit for cancelling capacitive coupling between the drive and sense electrodes.

Typically the capacitive cancelling circuit includes an inverting amplifier for coupling a signal generator output to a sensor input.

Typically the inverting amplifier applies a capacitance cancelling signal to the sensor input to thereby cancel any effective capacitance between the drive electrode and the sense electrode.

Typically an inverting amplifier output is coupled to the sensor input via at least one of:
 a) a resistor;
 b) a capacitor; and,
 c) an inductor.

Typically at least one of a resistor and capacitor are adjustable, thereby allowing a capacitance cancelling signal applied to the sensor input to be controlled.

Typically the electrode system includes an input capacitance cancelling circuit for cancelling an effective input capacitance at a sensor input.

Typically the electrode system includes a feedback loop for connecting a sensor output to the sensor input.

Typically the feedback loop includes at least one of:
 a) a resistor;
 b) a capacitor; and,
 c) an inductor.

Typically at least one of a resistor and capacitor are adjustable, thereby allowing a current flow from the sensor output to the sensor input to be controlled.

Typically the feedback loop applies an input capacitance cancelling signal to the sensor input to thereby cancel any effective capacitance at the sensor input.

In a third broad form the present invention seeks to provides apparatus for use in performing impedance measurements on a subject, wherein the apparatus includes:
 a) a number of electrode systems, and wherein each electrode system includes a signal generator and sensor, the signal generator being for applying a first signal to the subject and the sensor being for sensing a second signal across the subject; and,
 b) at number of leads for connecting the measuring device to the electrode systems, each lead including:
  i) at least two connections for connecting the measuring device and the signal generator, and the measuring device and the sensor; and,
  ii) a shield for each of the at least two connections, the shields being electrically connected, and connected to a reference voltage in each of the measuring device and the electrode system.

Typically the apparatus includes:
a) at least two electrode systems;
b) a measuring device for controlling the electrode systems to allow impedance measurements to be performed; and,
c) at least two leads for connecting the measuring device to the electrode systems.

Typically the leads are arranged in use to at least one of:
a) extend from the measuring device in different directions to thereby reduce inductive coupling therebetween; and,
b) minimise the lead length.

In a fourth broad form the present invention seeks to provides apparatus for use in performing impedance measurements on a subject, wherein the apparatus includes:
a) at least two electrode systems, and wherein each electrode system includes a signal generator and sensor, the signal generator being for applying a first signal to the subject and the sensor being for sensing a second signal across the subject; and,
b) a measuring device for controlling the electrode systems to allow impedance measurements to be performed; and,
c) at least two leads for connecting the measuring device to the electrode systems, the leads being arranged to at least one of:
  i) extend from the measuring device in different directions to thereby reduce inductive coupling therebetween; and,
  ii) minimise the lead length.

Typically the apparatus includes:
a) four electrode systems; and,
b) four leads extending from the measuring device in four different directions.

Typically each lead includes:
a) a first cable for coupling the measuring device to the signal generator to thereby allow the measuring device to control the signal generator to apply a first signal to the subject;
b) a second cable for coupling the measuring device to the signal generator to thereby allow the measuring device to determine a parameter relating to the first signal applied to the subject; and,
c) a third cable for coupling the measuring device to the sensor generator to thereby allow the measuring device to determine a voltage measured at the subject.

Typically the electrode system includes:
a) a first substrate having the signal generator and sensor mounted thereon; and,
b) a second substrate having at least two conductive pads mounted thereon, the conductive pads being for coupling the signal generator and the sensor to a subject in use.

In a fifth broad form the present invention seeks to provides a method for use in performing impedance measurements on a subject, wherein the method includes, in a processing system:
a) causing a first signal to be applied to the subject;
b) determining an indication of a second signal measured across the subject;
c) using the indication of the second signal to determine any imbalance; and,
d) if an imbalance exists:
  i) determining a modified first signal in accordance with the imbalance; and,
  ii) causing the modified first signal to be applied to the subject to thereby allow at least one impedance measurement to be performed.

In a sixth broad form the present invention seeks to provides a method for use in performing impedance measurements on a subject, wherein the method includes:
a) providing a pair of first and second electrodes on at least one wrist and at least one ankle of the subject;
b) coupling each pair of electrodes to an electrode system, the electrode system including a signal generator and sensor, the signal generator being for applying a first signal to the subject via the first electrode and the sensor being for sensing a second signal via the second electrode;
c) positioning a measuring device near the subject's knees, the measuring device being for controlling the electrode systems to allow impedance measurements to be performed; and,
d) coupling the measuring device to the electrode systems via respective leads such that the leads extend from the measuring device in different directions.

It will be appreciated that the broad forms of the invention may be used individually or in combination, and may be used for diagnosis of the presence, absence or degree of a range of conditions and illnesses, including, but not limited to oedema, pulmonary oedema, lymphodema, body composition, cardiac function, and the like.

BRIEF DESCRIPTION OF THE DRAWINGS

An example of the present invention will now be described with reference to the accompanying drawings, in which:—

FIGS. 10A and 10B are schematic diagrams of examples of electrode configurations used during balancing;

FIG. 10C is a schematic diagram of effective electrical models for the electrode arrangements of FIGS. 10A and 10B; and, FIG. 11 is a flow chart of a further example of an impedance measurement process;

DETAILED DESCRIPTION OF THE PREFERRED EMBODIMENTS

Figure 1:
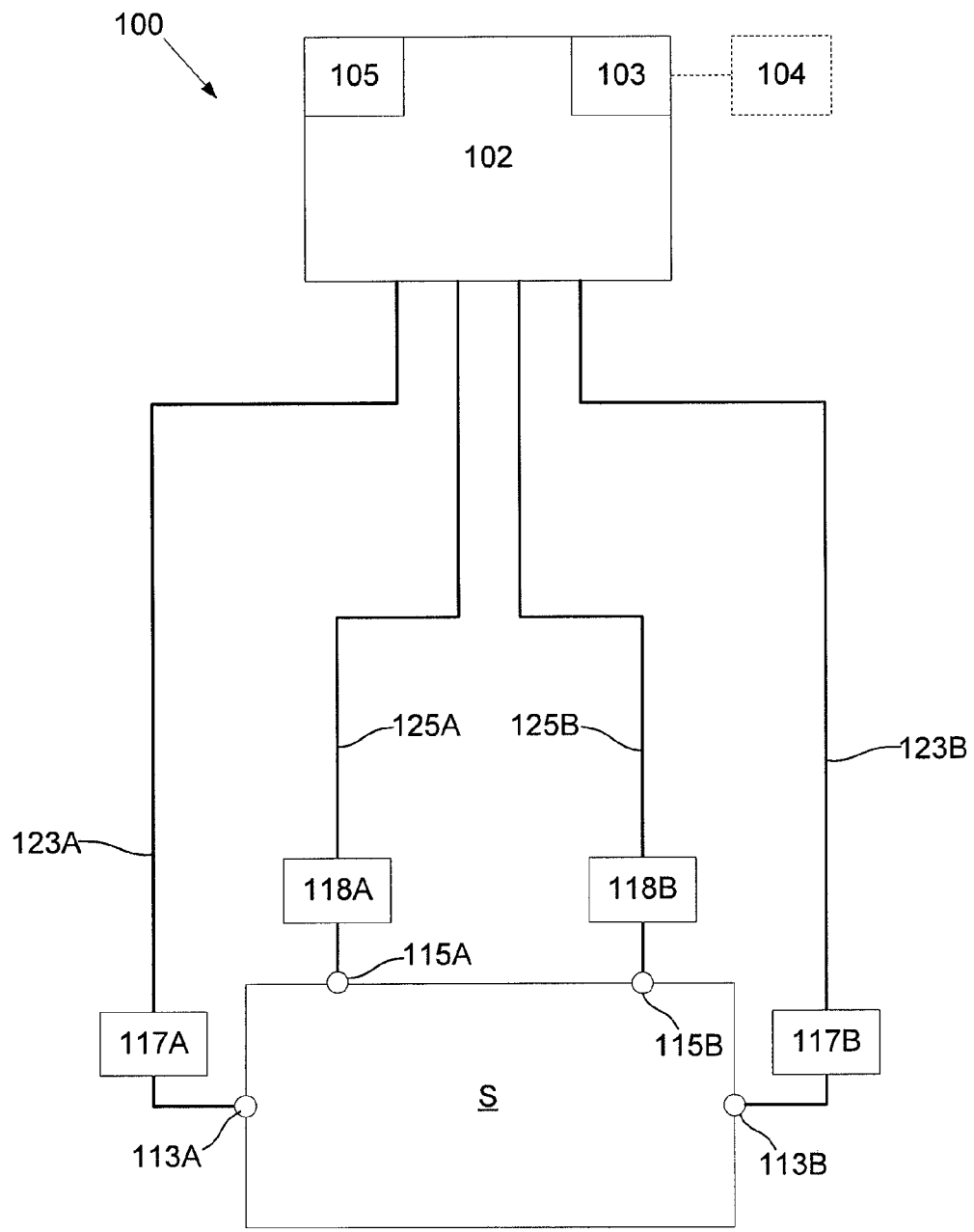
FIG. 1 is a schematic diagram of an example of an impedance measuring device.

An example of apparatus suitable for performing an analysis of a subject's bioelectric impedance will now be described with reference to FIG. 1.

As shown the apparatus includes a measuring device 100 including a processing system 102, connected to one or more signal generators 117A, 117B, via respective first leads 123A, 123B, and to one or more sensors 118A, 118B, via respective second leads 125A, 125B. The connection may be via a switching device, such as a multiplexer, although this is not essential.

In use, the signal generators 117A, 117B are coupled to two first electrodes 113A, 113B, which therefore act as drive electrodes to allow signals to be applied to the subject S, whilst the one or more sensors 118A, 118B are coupled to the second electrodes 115A, 115B, which act as sense electrodes, allowing signals across the subject S to be sensed.

The signal generators 117A, 117B and the sensors 118A, 118B may be provided at any position between the processing system 102 and the electrodes 113A, 113B, 115A, 115B, and may be integrated into the measuring device 100. However, in one example, the signal generators 117A, 117B and the sensors 118A, 118B are integrated into an electrode system, or another unit provided near the subject 5, with the leads 123A, 123B, 125A, 125B connecting the signal generators 117A, 117B and the sensors 118A, 118B to the processing system 102.

It will be appreciated that the above described system is a two channel device, used to perform a classical four-terminal impedance measurement, with each channel being designated by the suffixes A, B respectively. The use of a two channel device is for the purpose of example only, as will be described in more detail below.

An optional external interface 103 can be used to couple the measuring device 100, via wired, wireless or network connections, to one or more peripheral devices 104, such as an external database or computer system, barcode scanner, or the like. The processing system 102 will also typically include an I/O device 105, which may be of any suitable form such as a touch screen, a keypad and display, or the like.

In use, the processing system 102 is adapted to generate control signals, which cause the signal generators 117A, 117B to generate one or more alternating signals, such as voltage or current signals of an appropriate waveform, which can be applied to a subject S, via the first electrodes 113A, 113B. The sensors 118A, 118B then determine the voltage across or current through the subject S, using the second electrodes 115A, 115B and transfer appropriate signals to the processing system 102.

Accordingly, it will be appreciated that the processing system 102 may be any form of processing system which is suitable for generating appropriate control signals and at least partially interpreting the measured signals to thereby determine the subject's bioelectrical impedance, and optionally determine other information such as relative fluid levels, or the presence, absence or degree of conditions, such as oedema, lymphoedema, measures of body composition, cardiac function, or the like.

The processing system 102 may therefore be a suitably programmed computer system, such as a laptop, desktop, PDA, smart phone or the like. Alternatively the processing system 102 may be formed from specialised hardware, such as an FPGA (field programmable gate array), or a combination of a programmed computer system and specialised hardware, or the like, as will be described in more detail below.

In use, the first electrodes 113A, 113B are positioned on the subject to allow one or more signals to be injected into the subject S. The location of the first electrodes will depend on the segment of the subject S under study. Thus, for example, the first electrodes 113A, 113B can be placed on the thoracic and neck region of the subject S to allow the impedance of the chest cavity to be determined for use in cardiac function analysis. Alternatively, positioning electrodes on the wrist and ankles of a subject allows the impedance of limbs and/or the entire body to be determined, for use in oedema analysis, or the like.

Once the electrodes are positioned, one or more alternating signals are applied to the subject S, via the first leads 123A, 123B and the first electrodes 113A, 113B. The nature of the alternating signal will vary depending on the nature of the measuring device and the subsequent analysis being performed.

For example, the system can use Bioimpedance Analysis (BIA) in which a single low frequency signal (typically <50 kHz) is injected into the subject S, with the measured impedance being used directly in the assessment of relative intracellular and extracellular fluid levels. In contrast Bioimpedance Spectroscopy (BIS) devices utilise frequencies ranging from very low frequencies (4 kHz) to higher frequencies (1000 kHz), and can use as many as 256 or more different frequencies within this range, to allow multiple impedance measurements to be made within this range.

Thus, the measuring device 100 may either apply an alternating signal at a single frequency, at a plurality of frequencies simultaneously, or a number of alternating signals at different frequencies sequentially, depending on the preferred implementation. The frequency or frequency range of the applied signals may also depend on the analysis being performed.

In one example, the applied signal is generated by a voltage generator, which applies an alternating voltage to the subject S, although alternatively current signals may be applied. In one example, the voltage source is typically symmetrically arranged, with each of the signal generators 117A, 117B being independently controllable, to allow the signal voltage across the subject to be varied.

A voltage difference and/or current is measured between the second electrodes 115A, 115B. In one example, the voltage is measured differentially, meaning that each sensor 118A, 118B is used to measure the voltage at each second electrode 115A, 115B and therefore need only measure half of the voltage as compared to a single ended system.

The acquired signal and the measured signal will be a superposition of voltages generated by the human body, such as the ECG (electrocardiogram), voltages generated by the applied signal, and other signals caused by environmental electromagnetic interference. Accordingly, filtering or other suitable analysis may be employed to remove unwanted components.

The acquired signal is typically demodulated to obtain the impedance of the system at the applied frequencies. One suitable method for demodulation of superposed frequencies is to use a Fast Fourier Transform (FFT) algorithm to transform the time domain data to the frequency domain. This is typically used when the applied current signal is a superposition of applied frequencies. Another technique not requiring windowing of the measured signal is a sliding window FFT.

In the event that the applied current signals are formed from a sweep of different frequencies, then it is more typical to use a signal processing technique such as multiplying the measured signal with a reference sine wave and cosine wave derived from the signal generator, or with measured sine and cosine waves, and integrating over a whole number of cycles. This process, known variously as quadrature demodulation or synchronous detection, rejects all uncorrelated or asynchronous signals and significantly reduces random noise.

Other suitable digital and analogue demodulation techniques will be known to persons skilled in the field.

In the case of BIS, impedance or admittance measurements are determined from the signals at each frequency by comparing the recorded voltage and the current through the subject. The demodulation algorithm can then produce amplitude and phase signals at each frequency.

As part of the above described process, the distance between the second electrodes 115A, 115B may be measured and recorded. Similarly, other parameters relating to the subject may be recorded, such as the height, weight, age, sex, health status, any interventions and the date and time on which they occurred. Other information, such as current medication, may also be recorded. This can then be used in performing further analysis of the impedance measurements, so as to allow determination of the presence, absence or degree of oedema, to assess body composition, or the like.

The accuracy of the measurement of impedance can be subject to a number of external factors. These can include, for example, the effect of capacitive coupling between the subject and the surrounding environment, the leads and the subject, the electrodes, or the like, which will vary based on factors such as lead construction, lead configuration, subject position, or the like. Additionally, there are typically variations in the impedance of the electrical connection between the electrode surface and the skin (known as the "electrode impedance"), which can depend on factors such as skin moisture levels, melatonin levels, or the like. A further source of error is the presence of inductive coupling between different electrical conductors within the leads, or between the leads themselves.

Such external factors can lead to inaccuracies in the measurement process and subsequent analysis and accordingly, it is desirable to be able to reduce the impact of external factors on the measurement process.

One form of inaccuracy that can arise is caused by the voltages across the subject being unsymmetrical, a situation referred to as an "imbalance". Such a situation results in a significant signal voltage at the subject's body centre, which in turn results in stray currents arising from parasitic capacitances between the subject's torso and the support surface on which the subject is provided.

The presence of an imbalance, where the voltage across the subject is not symmetrical with respect to the effective centre of the subject, leads to a "common mode" signal, which is effectively a measure of the signal at the subject S that is unrelated to the subject's impedance.

To help reduce this effect, it is therefore desirable for signals to be applied to the subject S that they result in a symmetrical voltage about the subject's body centre. As a result, a reference voltage within the subject S, which is equal to a reference voltage of the measurement apparatus, will be close to the effective body centre of the subject, as considered relative to the electrode placement. As the measuring device reference voltage is typically ground, this results in the body centre of the subject S being as close to ground as possible, which minimises the overall signal magnitude across the subject's torso, thereby minimising stray currents.

In one example, a symmetrical voltage about the sensing electrodes can be achieved by using a symmetrical voltage source, such as a differential bidirectional voltage drive scheme, which applies a symmetrical voltage to each of the drive electrodes 113A, 113B. However, this is not always effective if the contact impedances for the two drive electrodes 113A, 113B are unmatched, or if the impedance of the subject S varies along the length of the subject S, which is typical in a practical environment.

In one example, the apparatus overcomes this by adjusting the differential voltage drive signals applied to each of the drive electrodes 113A, 113B, to compensate for the different electrode impedances, and thereby restore the desired symmetry of the voltages across the subject S. This process is referred to herein as balancing and in one example, helps reduce the magnitude of the common mode signal, and hence reduce current losses caused by parasitic capacitances associated with the subject.

The degree of imbalance, and hence the amount of balancing required, can be determined by monitoring the signals at the sense electrodes 115A, 115B, and then using these signals to control the signal applied to the subject via the drive electrodes 113A, 113B. In particular, the degree of imbalance can be calculated by determining an additive voltage from the voltages detected at the sense electrodes 115A, 115B.

In one example process, the voltages sensed at each of the sense electrodes 115A, 115B are used to calculate a first voltage, which is achieved by combining or adding the measured voltages. Thus, the first voltage can be an additive voltage (commonly referred to as a common mode voltage or signal) which can be determined using a differential amplifier.

In this regard, a differential amplifier is typically used to combine two sensed voltage signals $V_a$, $V_b$, to determine a second voltage, which in one example is a voltage differential $V_a - V_b$ across the points of interest on the subject S. The voltage differential is used in conjunction with a measurement of the current flow through the subject to derive impedance values. However, differential amplifiers typically also provide a "common mode" signal $(V_a + V_b)/2$, which is a measure of the common mode signal.

Whilst differential amplifiers include a common mode rejection capability, this is generally of only finite effect and typically reduces in effectiveness at higher frequencies, so a large common mode signal will produce an error signal superimposed on the differential signal.

The error caused by common mode signals can be minimised by calibration of each sensing channel. In the ideal case where both inputs of a differential amplifier are perfectly matched in gain and phase characteristics and behave linearly with signal amplitude, the common mode error will be zero. In one example, the two sensing channels of the differential amplifier are digitised before differential processing. It is therefore straightforward to apply calibration factors independently to each channel to allow the characteristics to be matched to a high degree of accuracy, thereby achieving a low common mode error.

Accordingly, by determining the common mode signal, the applied voltage signals can be adjusted, for example by adjusting the relative magnitude and/or phase of the applied signals, to thereby minimise the common mode signal and substantially eliminate any imbalance.

An example of the operation of the apparatus of FIG. 1 to perform this will now be described with reference to FIG. 2.

At step 200, a first signal is applied to the subject S, with a second signal measured across the subject S being determined at step 210. This will typically be achieved using the techniques outlined above. Accordingly, the processing system 102 will cause the signal generators 117A, 117B to generate the first signal, which is typically applied to the subject S via the first electrodes 113A, 113B. Similarly the second signal will be sensed by the sensors 118A, 118B, via the second electrodes 115A, 115B, with an indication of the second signal being provided to the processing system 102.

At step 220, an imbalance is determined by the processing system 102 using the second signal sensed at the second electrodes 115A, 115B, which in one example represents a common mode signal.

At step 230, the measuring device optionally adjusts the first signal applied to the subject S, so as to reduce the imbalance and hence the magnitude of the common mode signal. Thus, the magnitude of the signal applied at either one of the first electrodes 113A, 113B can be adjusted, for example by increasing or decreasing the relative signal magnitudes and/or altering the relative signal phases, so as to balance the signal within the subject and centralise the position of the reference voltage within the subject relative to the electrode positioning.

At step 240, the measuring device can then determine the signal applied to the subject and the voltages measured at the electrodes 113A, 113B, thereby allowing an impedance to be determined at step 250.

As the position of the reference voltage within the subject S is impedance dependent, the imbalance will typically vary depending on the frequency of the applied signal. Accordingly, in one example, it is typical to determine the imbalance and adjust the applied signal at each applied frequency. However, this may depend on the preferred implementation.

Figure 3:
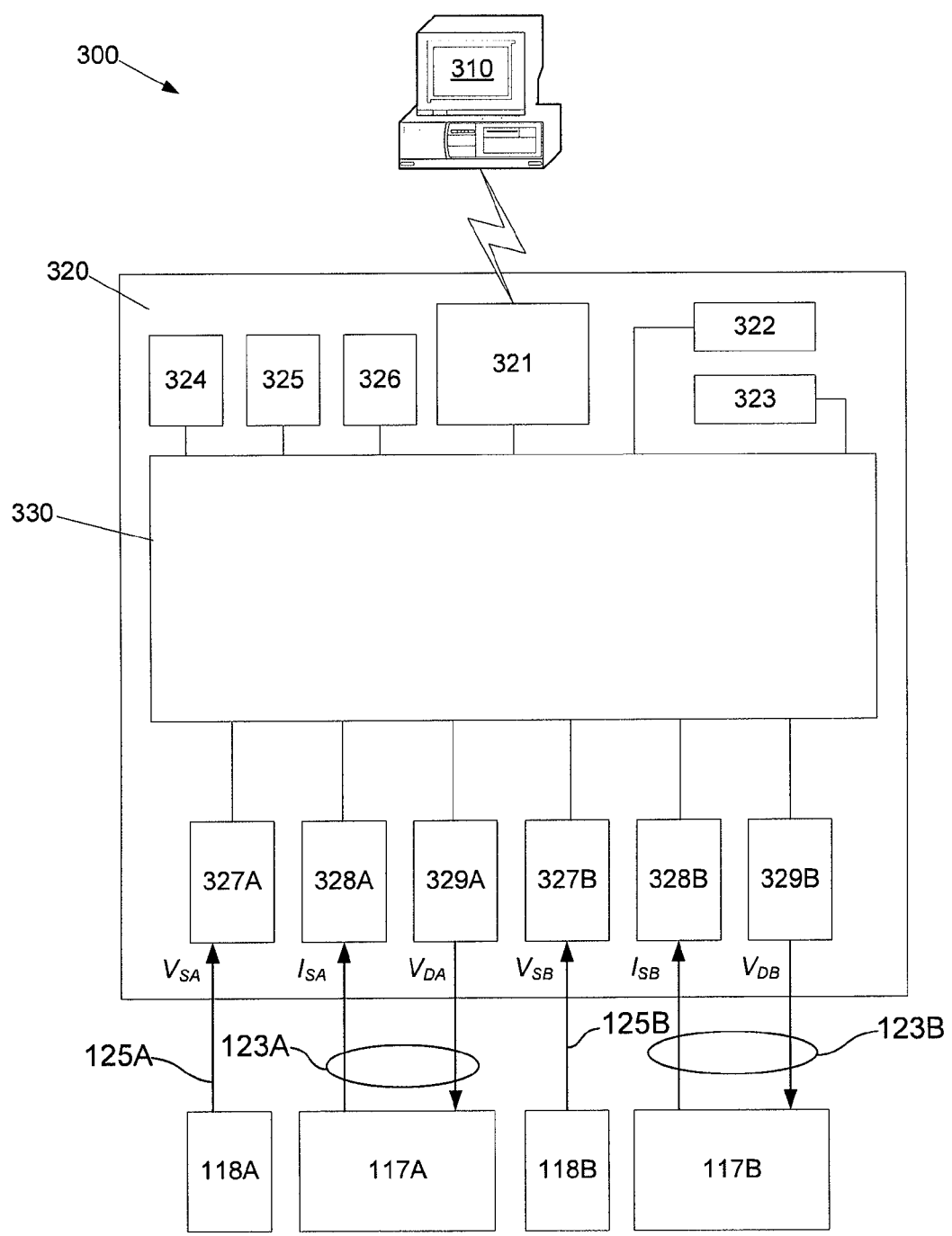
FIG. 3 is a schematic diagram of a second example of an impedance measuring device.

A specific example of the apparatus will now be described in more detail with respect to FIG. 3.

In this example, the measuring system 300 includes a computer system 310 and a separate measuring device 320. The measuring device 320 includes a processing system 330 coupled to an interface 321 for allowing wired or wireless communication with the computer system 310. The processing system 330 may also be optionally coupled to one or more stores, such as different types of memory, as shown at 322, 323, 324, 325, 326.

In one example, the interface is a Bluetooth stack, although any suitable interface may be used. The memories can include a boot memory 322, for storing information required by a boot-up process, and a programmable serial number memory 323, that allows a device serial number to be programmed. The memory may also include a ROM (Read Only Memory) 324, flash memory 325 and EPROM (Electronically Programmable ROM) 326, for use during operation. These may be used for example to store software instructions and to store data during processing, as will be appreciated by persons skilled in the art.

A number of analogue to digital converters (ADCs) 327A, 327B, 328A, 328B and digital to analogue converters (DACs) 329A, 329B are provided for coupling the processing system 330 to the sensors 118A, 118B and the signal generators 117A, 117B, as will be described in more detail below.

A controller (not shown), such as a microprocessor, microcontroller or programmable logic device, may also be provided to control activation of the processing system 330, although more typically this is performed by software commands executed by the processing system 330.

Figure 4:
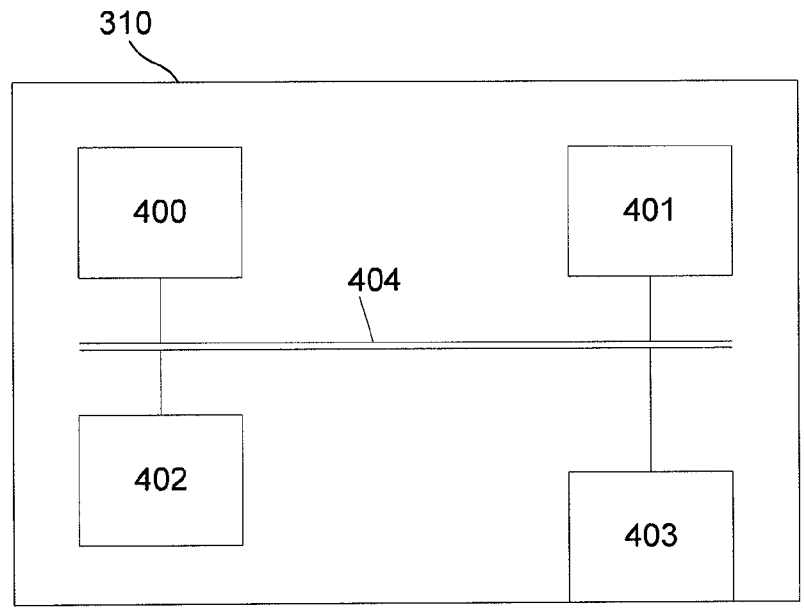
FIG. 4 is a schematic diagram of an example of a computer system.

An example of the computer system 310 is shown in FIG. 4. In this example, the computer system 310 includes a processor 400, a memory 401, an input/output device 402 such as a keyboard and display, and an external interface 403 coupled together via a bus 404, as shown. The external interface 403 can be used to allow the computer system to communicate with the measuring device 320, via wired or wireless connections, as required, and accordingly, this may be in the form of a network interface card, Bluetooth stack, or the like.

In use, the computer system 310 can be used to control the operation of the measuring device 320, although this may alternatively be achieved by a separate interface provided on the measuring device 300. Additionally, the computer system can be used to allow at least part of the analysis of the impedance measurements to be performed.

Accordingly, the computer system 310 may be formed from any suitable processing system, such as a suitably programmed PC, Internet terminal, lap-top, hand-held PC, smart phone, PDA, server, or the like, implementing appropriate applications software to allow required tasks to be performed.

In contrast, the processing system 330 typically performs specific processing tasks, to thereby reduce processing requirements on the computer system 310. Thus, the processing system typically executes instructions to allow control signals to be generated for controlling the signal generators 117A, 117B, as well as the processing to determine instantaneous impedance values.

In one example, the processing system 330 is formed from custom hardware, or the like, such as a Field Programmable Gate Array (FPGA), although any suitable processing module, such as a magnetologic module, may be used.

In one example, the processing system 330 includes programmable hardware, the operation of which is controlled using instructions in the form of embedded software instructions. The use of programmable hardware allows different signals to be applied to the subject S, and allows different analysis to be performed by the measuring device 320. Thus, for example, different embedded software would be utilised if the signal is to be used to analyse the impedance at a number of frequencies simultaneously as compared to the use of signals applied at different frequencies sequentially.

The embedded software instructions used can be downloaded from the computer system 310. Alternatively, the instructions can be stored in memory such as the flash memory 325 allowing the instructions used to be selected using either an input device provided on the measuring device 320, or by using the computer system 310. As a result, the computer system 310 can be used to control the instructions, such as the embedded software, implemented by the processing system 330, which in turn alters the operation of the processing system 330.

Additionally, the computer system 310 can operate to analyse impedance determined by the processing system 330, to allow biological parameters to be determined.

Whilst an alternative arrangement with a single processing system may be used, the division of processing between the computer system 310 and the processing system 330 can provide some benefits.

Firstly, the use of the processing system 330 allows the custom hardware configuration to be adapted through the use of appropriate embedded software. This in turn allows a single measuring device to be used to perform a range of different types of analysis.

Secondly, this vastly reduces the processing requirements on the computer system 310. This in turn allows the computer system 310 to be implemented using relatively straightforward hardware, whilst still allowing the measuring device to perform sufficient analysis to provide interpretation of the impedance. This can include for example displaying information such as relative fluid levels, body composition parameters, a "Wessel" plot, or other indicators, as well as using the impedance values to determine parameters relating to cardiac function, the presence, absence or degree of lymphoedema, oedema, or the like.

Thirdly, this allows the measuring device 320 to be updated. Thus for example, if an improved analysis algorithm is created, or an improved current sequence determined for a specific impedance measurement type, the measuring device can be updated by downloading new embedded software via flash memory 325 or the external interface 321.

In use, the processing system 330 generates digital control signals, indicative of the voltage drive signals $V_{DA}$, $V_{DB}$ to be applied via the drive electrodes 113A, 113B, which are converted to analogue control signals by the DACs 329. The analogue control signals are transferred to the signal generators 117, allowing voltage drive signals $V_{DA}$, $V_{DB}$ to be generated by each of the signal generators 117A, 117B.

Analogue signals representing sensed current signals $I_{SA}$, $I_{SB}$, induced by the voltage drive signals $V_{DA}$, $V_{DB}$ are received from the signal generators 117A, 117B and digitised by the ADCs 328A, 328B. Similarly, analogue signals representing sensed voltages $V_{SA}$, $V_{SB}$ measured at the second electrodes 115A, 115B are received from the sensors 118A, 118B and digitised by the ADCs 327A, 327B. The digital signals can then be returned to the processing system 330 for preliminary analysis.

In this example, a respective set of ADCs 327, 328, and DACs 329 are used for each of two channels, as designated by the reference numeral suffixes A, B respectively. This allows each of the signal generators 117A, 117B to be controlled independently and for the sensors 118A, 118B to be used to detect signals from the electrodes 115A, 115B separately. This therefore represents a two channel device, each channel being designated by the reference numerals A, B. It will be appreciated that similarly, voltage drive signals $V_D$, sensed current signals $I_S$, and sensed voltage signals $V_S$ can also similarly be identified by a suffix A, B, representing the respective channel.

In practice, any number of suitable channels may be used, depending on the preferred implementation. Thus, for example, it may be desirable to use a four channel arrangement, in which four drive and four sense electrodes are provided, with a respective sense electrode and drive electrode pair 113, 115 being coupled to each limb. In this instance, it will be appreciated that an arrangement of eight ADCs 327, 328, and four DACs 329 could be used, so each channel has respective ADCs 327, 328, and DACs 329. Alternatively, other arrangements may be used, such as through the inclusion of a multiplexing system for selectively coupling a two-channel arrangement of ADCs 327, 328, and DACs 329 to a four channel electrode arrangement, as will be appreciated by persons skilled in the art.

Additional channels may also be provided for performing additional measurements at other locations on the subject, such as to allow direct measurement of voltages at the shoulder, the hip or a variety of abdominal locations.

Figure 5:
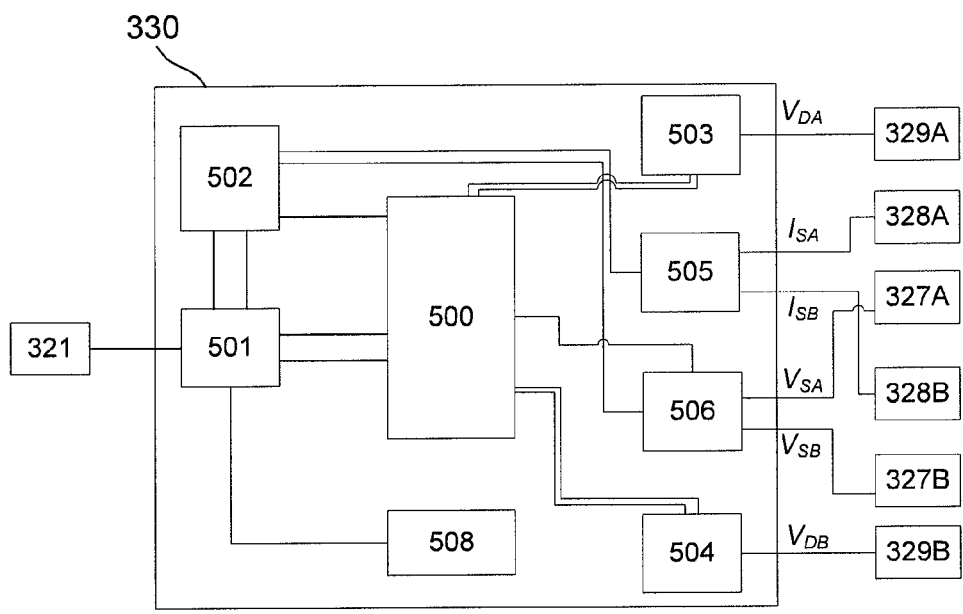
FIG. 5 is a schematic of an example of the functionality of the processing system of FIG. 3.

An example of the functionality implemented by the processing system 330 will now be described with reference to FIG. 5. In this example the processing system 330 implements the functionality using appropriate software control, although any suitable mechanism may be used.

In this example the processing system 330 includes a timing and control module 500, a messaging module 501, an analysis module 502, sine wave look up tables (LUTs) 503, 504, a current module 505, and a voltage module 506.

In use, the processing system 330 receives information representing the frequency and amplitude of signals to be applied to the subject S from the computer system 310, via the external interface 321. The timing and control module 500 uses this information to access the LUTs 503, 504, which in turn cause a digital sine wave signal to be produced based on the specified frequency and amplitude. The digital control signals are transferred to the DAC's 329A, 329B, to thereby allow analogue control signals indicative of the voltage drive signals $V_{DA}$, $V_{DB}$ to be produced.

Measured analogue voltage and current signals $V_{SA}$, $V_{SB}$, $I_{SA}$, $I_{SB}$ are digitised by the ADC's 327, 328 and provided to the current and voltage modules 505, 506. This allows the processing system 330 to determine the current flow by having the current module 505 determine the total current flow through the subject using the two current signals $I_{SA}$, $I_{SB}$, with an indication of this being provided to the analysis module 502. The voltage module 506, which is typically in the form of a differential voltage amplifier, or the like, operates to determine a differential voltage, which is also transferred to the analysis module 502, allowing the analysis module to determine impedance values using the current and differential voltage signals.

In addition to this, the voltage module 506 determines a common mode signal, which is returned to the timing and control module 500. This allows the timing and control module 500 to determine any imbalance in the voltage sensed at the subject S, which as mentioned above is indicative of the reference voltage not being positioned centrally within the subject S, with respect to the electrodes.

If the degree of imbalance is unacceptable the timing and control module 500 can adjust the relative amplitude and/or phase of the sine waves representing the voltage drive signals $V_{DA}$, $V_{DB}$ as will be described below, allowing a new differential voltage, hence indication of any imbalance, to be determined.

Once the imbalance is determined to be acceptable the timing and control module 500 can provide an indication of this to the analysis module 502, allowing this to use appropriate analysis, such as phase quadrature extraction, to determine a ratio and phase difference for the measured impedance, based on the current flow through the subject and the differential voltage signals. The ratio and phase can then be transferred to the messaging module 510 allowing an indication of measured impedance to be provided to the computer system 310 via the interface 321.

The processing system 330 may also implement a signal level fault detection module 508. This monitors the magnitude of signals applied to the subject to determine if these are within acceptable threshold levels. If not, the fault detection module 508 can cause a message to be transferred to the computer system 310 to allow the process to be halted or to allow an alert to be generated.

During this process, any measurements made, including raw current and voltage signals, may be stored in a suitable one of the memories 322, 323, 324, 325, 326, or otherwise output, allowing this to be used to monitor device operation. This can be used in performing diagnostics, as well as calibration of the device.

Figure 6A:
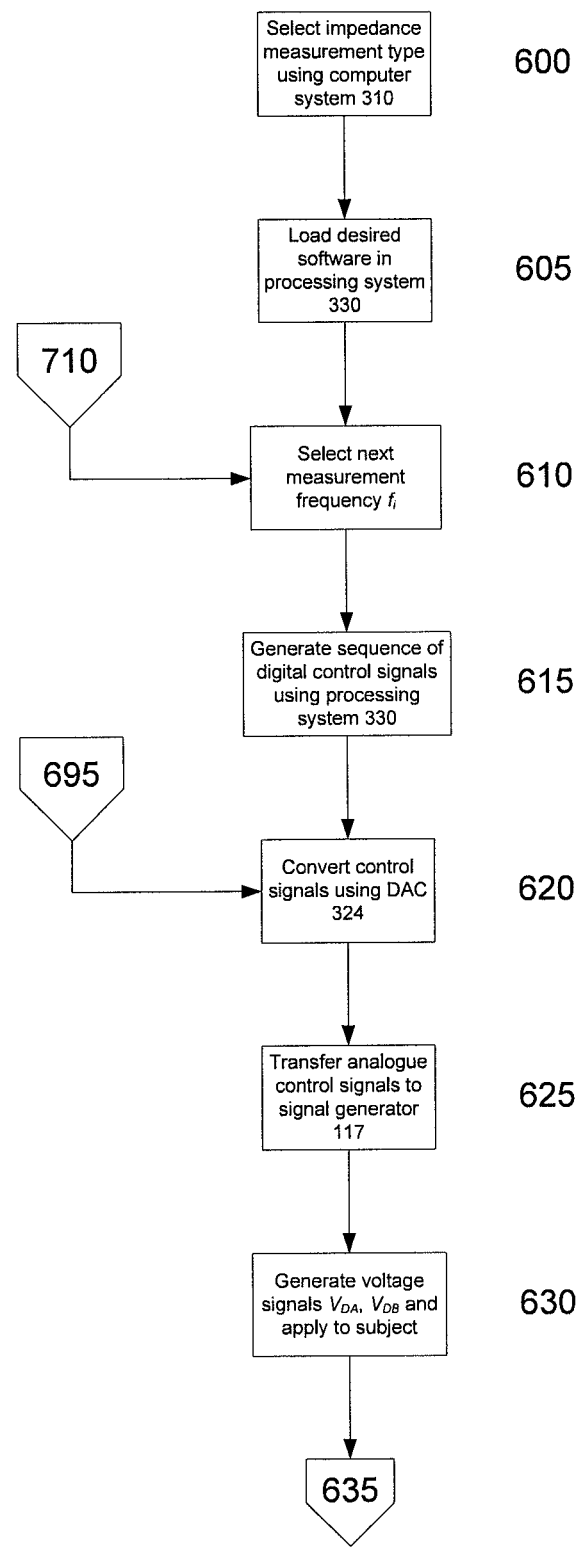
FIGS. 6A to 6C are a flowchart of a second example of a process for performing impedance measurements.
Figure 6B:
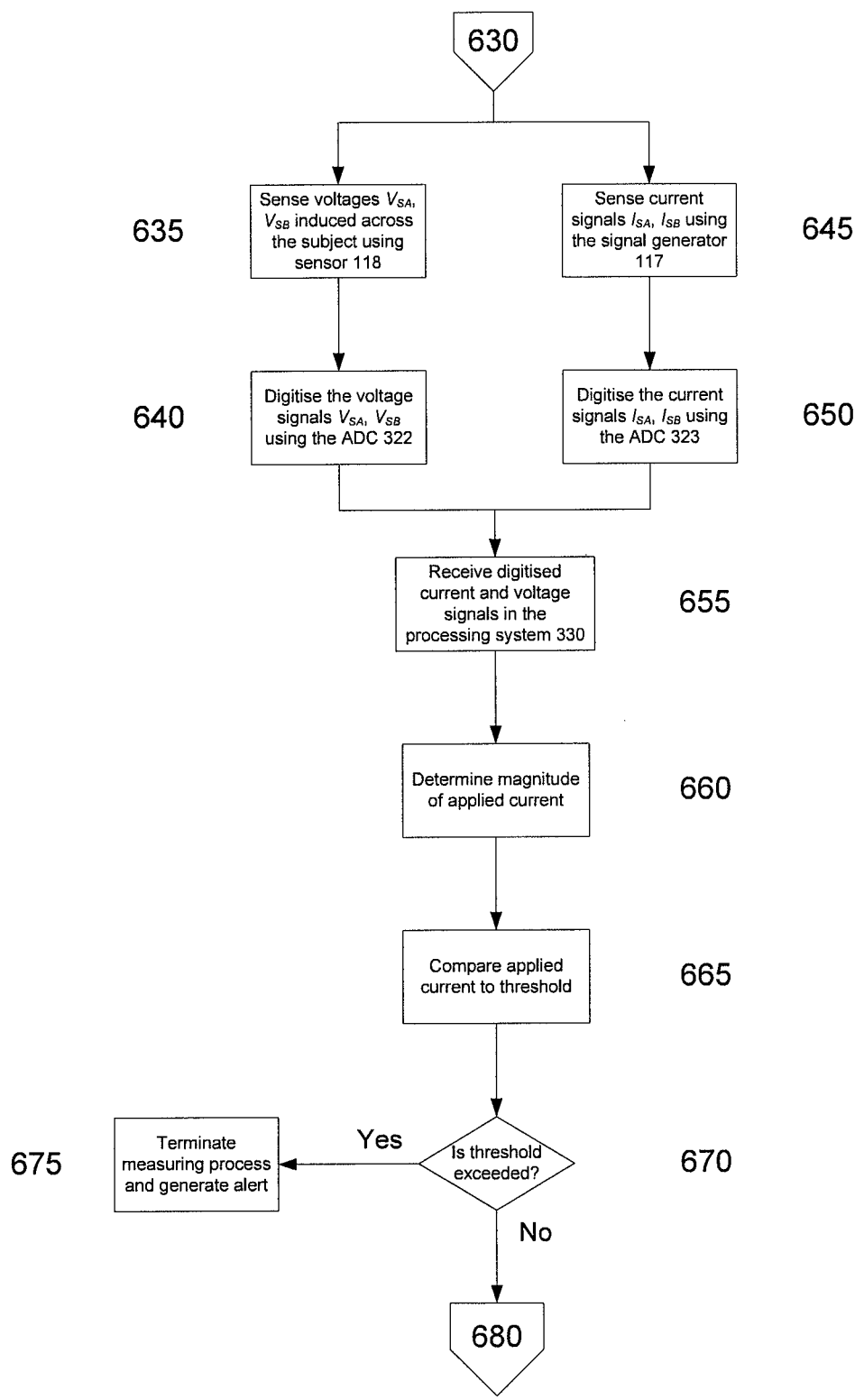
Figure 6C:
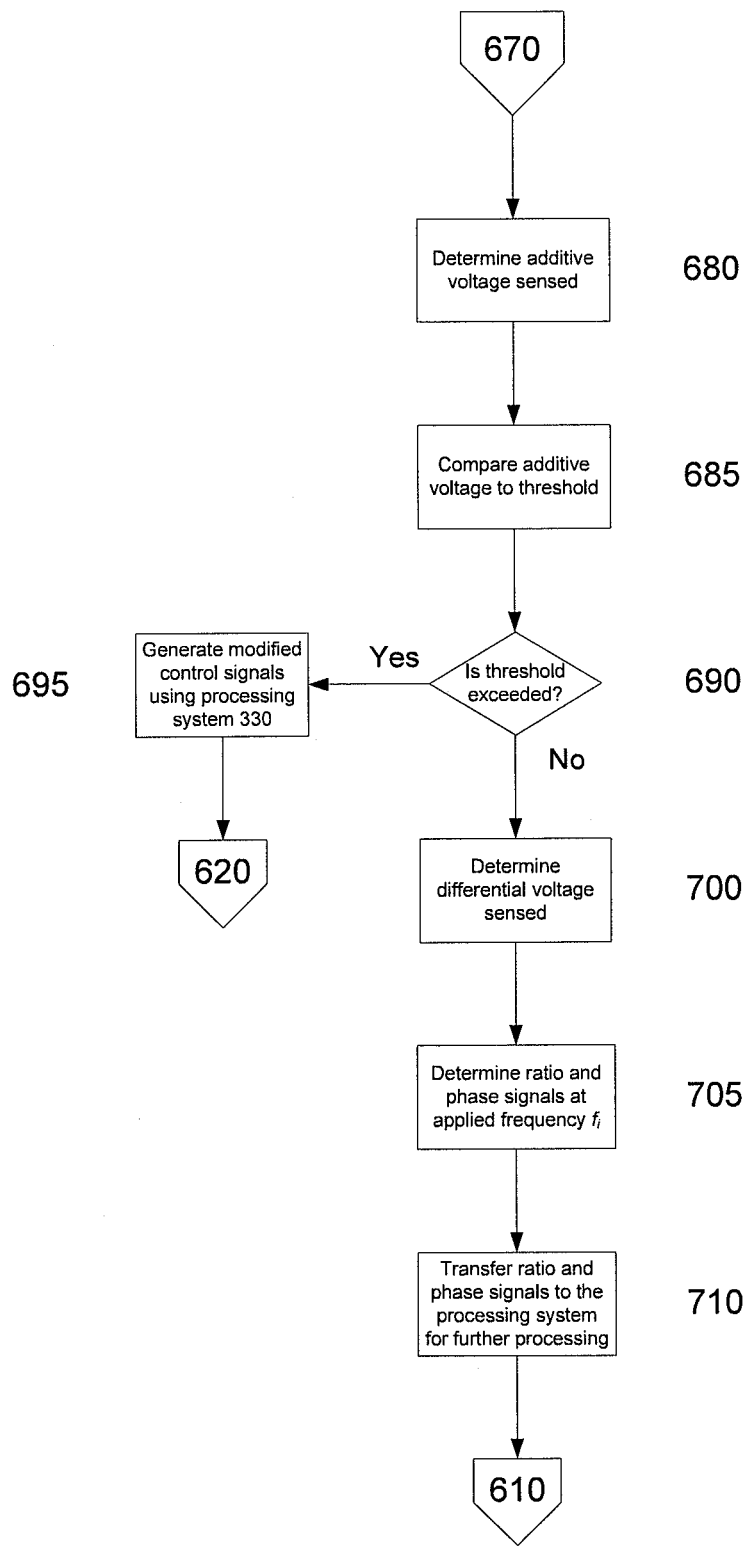

An example of the process for performing impedance measurements will now be described with reference to FIGS. 6A to 6C.

At step 600 the computer system 310 is used to select an impedance measurement type, with this triggering the computer system 310 to cause desired instructions, such as embedded software, to be implemented by the processing system 330. It will be appreciated that this may be achieved in a number of manners, such as by downloading required embedded software from the computer system 310 to the processing system 330 or alternatively by having the processing system 330 retrieve relevant embedded software from internal memory or the like.

At step 610 the computer system 310 or the processing system 330 selects a next measurement frequency $f_i$, allowing the processing system 330 to generate a sequence of digital voltage control signals at step 615, as described above. The digital control signals are converted to analogue control signals indicative of the voltage drive signals $V_{DA}$, $V_{DB}$ using the DACs 329A, 329B at step 620. This allows the analogue control signals to be provided to each of the signal generators 117A, 117B at step 625, causing each signal generator 117A, 117B to generate respective voltage drive signals $V_{DA}$, $V_{DB}$ and apply these to the subject S at step 630, via the respective drive electrodes 113A, 113B.

At step 635 the voltage induced across the subject is determined by having the sensors 118A, 118B sense voltages $V_{SA}$, $V_{SB}$ at the sense electrodes, 115A, 115B, with the sensed voltage signals $V_{SA}$, $V_{SB}$ being digitised by the corresponding ADC 327A, 327B at step 640. At step 645 current signals $I_{SA}$, $I_{SB}$, caused by application of the voltage drive signals $V_{DA}$, $V_{DB}$, are determined using the signal generators 117A, 117B. An indication of the current signals $I_{SA}$, $I_{SB}$ are transferred to the ADCs 328A, 328B for digitisation at step 650.

At step 655 the digitised current and voltage signals $I_{SA}$, $I_{SB}$, $V_{SA}$, $V_{SB}$ are received by the processing system 330 allowing the processing system 330 to determine the magnitude of the applied current $I_S$ at step 660. This may be performed using the current addition module 505 in the above described functional example of FIG. 5, allowing the fault detection module 508 to compare the total current flow $I_S$ through the subject to a threshold at step 665. If it is determined that the threshold has been exceeded at step 670 then the process may terminate with an alert being generated at step 675.

This situation may arise, for example, if the device is functioning incorrectly, or there is a problem with connections of electrodes to the subject, such as if one is not in correct electrical contact with the subject's skin. Accordingly, the alert can be used to trigger a device operator to check the electrode connections and/or device operation to allow any problems to be overcome. It will be appreciated, that any suitable form of corrective action may be taken such as attempting to restart the measurement process, reconnecting the electrodes to the subject S, reducing the magnitude of the current through the subject, or the like.

At step 680 the processing system 330 operates to determine a common mode voltage based on the amplitude of the sensed voltages $V_{SA}$, $V_{SB}$ sensed at each of the electrodes 115A, 115B, and this is typically achieved using the voltage processing module 506 in the above functional example. The common mode voltage or common mode signal is then used to determine any imbalance at step 685.

At step 690 an assessment is made as to whether the imbalance is acceptable. This may be achieved in any one of a number of ways, such as by comparing the amplitude of the common mode signal to a threshold, or the like. The threshold will generally be previously determined and stored in one of the memories 324, 325, 326, for example during device manufacture or calibration.

In the event that the imbalance is deemed to not be acceptable, then at step 695 the processing system 330 modifies the digital control signals representing the voltage drive signals $V_{DA}$, $V_{DB}$ to reduce the imbalance. This is typically achieved by having the processing system 330 implement an algorithm that adjusts the applied voltage drive signals $V_{DA}$, $V_{DB}$ to maintain the common mode voltage at the centre of the body as close to the device reference voltage as possible. This is generally achieved by adjusting the amplitude and/or phase of the voltage drive signals $V_{DA}$, $V_{DB}$ applied to the subject, using the algorithm. The nature of this adjustment will depend on the nature of the imbalance, and an example algorithm will be described in more detail below.

The process can then return to step 620 to allow the modified digital control signals to be converted to analogue signals using DACs 324, with modified voltage drive signals $V_{DA}$, $V_{DB}$ being applied to the drive electrodes 113A, 113B. This process is repeated until an acceptable balance is achieved.

Once an acceptable balance is achieved, the processing system 330 operates to determine the differential voltage sensed across the subject at step 700. In the functional example described above with respect to FIG. 5, this can be achieved using the differential voltage module 506.

At step 705 the processing module 330 operates to determine ratio and phase signals, representing the impedance of the subject S, at the applied frequency $f_i$ using the current and differential voltage signals. In the above functional example, this can be performed using the analysis module, and some form of signal analysis, such as phase quadrature analysis, depending on the preferred implementation. At step 710, an indication of the ratio and phase signals are sent to the computer system 310 for further processing.

Once this is completed the process may return to step 610 to allow the process to be repeated at a next measurement frequency $f_i$ otherwise if all required frequencies are complete, the measurement process can terminate, allowing the computer system 310 to analyse the impedance measurements, and determine required information, such as any biological indicators, impedance parameters, or the like. The manner in which this is achieved will depend on the type of analysis being performed.

Accordingly, it will be appreciated that by repeating the above described process this allows a number of impedance measurements to be performed over a range of different frequencies. Furthermore, prior to at least one, and more typically, to each measurement, a check can be performed to ensure that the common mode of the subject and the device are approximately matched, thereby reducing inaccuracies in the measurement procedure.

Figure 7A:
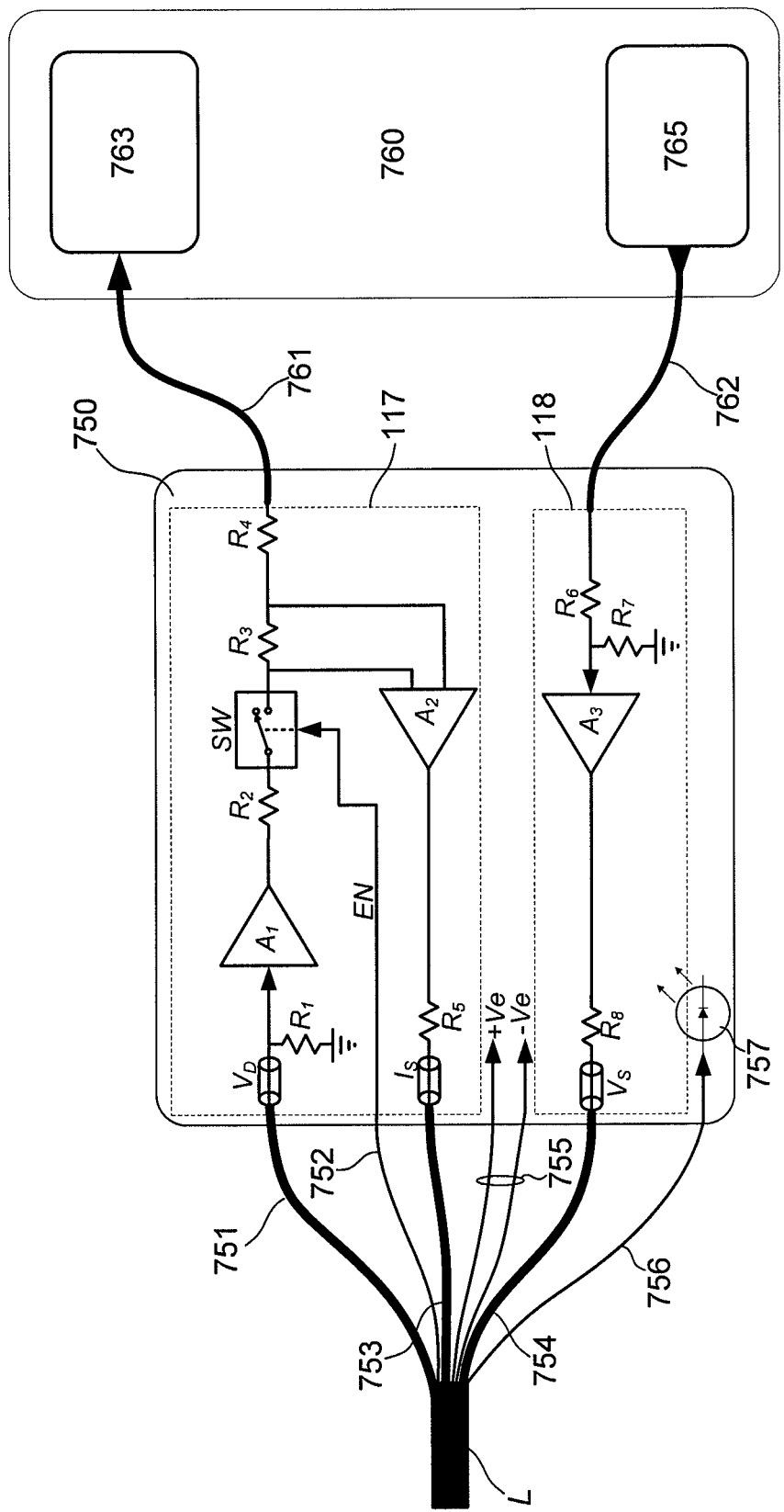
FIG. 7A is a schematic diagram of an example of an electrode system incorporating a signal generator and a sensor.

FIG. 7A is an example of an electrode system for a single one of the channels, which incorporates both a drive electrode 113 and sense electrode 115.

The electrode system incorporates a first substrate 750, such as a printed circuit board (PCB), or the like, having the respective signal generator 117 and sensor 118 mounted thereon. The general functionality of the signal generator 117 and sensor 118 are represented by the components shown. In practice a greater number of components may be used in a suitable arrangement, as would be appreciated by persons skilled in the art, and the components shown are merely intended to indicate the functionality of the signal generator and the sensor 117, 118.

The substrate 750 and associated components may be provided in a suitable housing to protect them during use, as will be appreciated by persons skilled in the art.

The signal generator 117 and the sensor 118 are coupled via respective cables 761, 762 to conductive pads 763, 765, which may be mounted on a second substrate 760, and which form the first and second electrodes 113, 115, respectively. It will be appreciated that in use, the cables 761, 762 may include clips or the like, to allow the conductive pads to be easily replaced after use.

As will be appreciated, the conductive pads are typically formed from a silver pad, having a conductive gel, such as silver/silver chloride gel, thereon. This ensures good electrical contact with the subject S.

The conductive pads may be mounted on the substrate 760, so as to ensure that the conductive pads 763, 765 are positioned a set distance apart in use, which can help ensure measurement consistency. Alternatively the conductive pads 763, 765 can be provided as separate disposable conductive pads, coupled to the first substrate 750 by cables 761, 762. Other suitable arrangements may also be used.

In one example, the substrate 760 is formed from a material that has a low coefficient of friction and/or is resilient, and/or has curved edges to thereby reduce the chances of injury when the electrodes are coupled to the subject. The substrate 760 is also typically arranged to facilitate electrical contact between the conductive pads 763, 765 and the subject's skin at the typical measurement sites, such as the wrist and ankle. This can be achieved by providing a substrate 760 that adapts to, or is shaped to conform with the irregular shapes and angles of the anatomy.

In this example, the signal generator 117 includes an amplifier $A_1$ having an input coupled to a cable 751. The input is also coupled to a reference voltage, such as ground, via a resistor $R_1$. An output of the amplifier $A_1$ is connected via a resistor $R_2$, to a switch SW, which is typically a CMOS (complementary metal-oxide semiconductor) switch or a relay that is used to enable the voltage source. The switch SW is controlled via enabling signals EN received from the processing system 330 via a cable 752.

The switch SW is in turn coupled via two resistors $R_3$, $R_4$, arranged in series, and then, via the cable 761, to the conductive pad 763. A second amplifier $A_2$ is provided with inputs in parallel with the first of the two series resistor $R_3$ and with an output coupled via a resistor $R_5$, to a cable 753.

Figure 2:
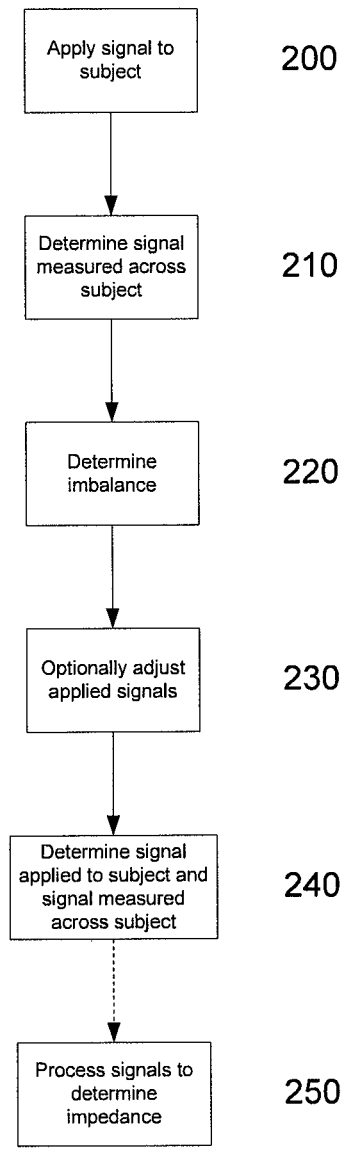
FIG. 2 is a flowchart of an example of a process for performing impedance measuring.

It will be appreciated from the above that the cables 751, 752, 753 therefore forms the lead 123 of FIG. 1. A range of different resistor values may be used, but in one example, the resistors have values of $R_1=R_2=R_5=50\Omega$, and $R_3=R_4=100\Omega$.

The sensor 118 generally includes an amplifier $A_3$ having an input connected via a resistor $R_6$, to the cable 762. The input is also coupled via a resistor $R_7$, to a reference voltage such as a ground. An output of the amplifier $A_3$ is coupled to a cable 754, via a resistor $R_7$.

It will be appreciated from the above that the cable 754 therefore forms the lead 125 of FIG. 1. A range of different resistor values may be used, but in one example, the resistors have values of $R_6=100\Omega$, $R_7=10$ M$\Omega$ and, $R_8=50\Omega$.

Optional power cables 755 can be provided for supplying power signals +Ve, −Ve, for powering the signal generator 117 and the sensor 118, although alternatively an on board power source such as a battery, may be used. Additionally, a cable 756 may be provided to allow an LED 757 to be provided on the substrate 750. This can be controlled by the processing system 330, allowing the operating status of the electrode system to be indicated.

Operation of the signal generator 117 and the sensor 118 will now be described in more detail. For the purpose of this explanation, the voltage drive signal, current signal and sensed voltage will be generally indicated as $V_D$, $I_S$, $V_S$, and in practice, these would be equivalent to respective ones of the voltage drive signals, current signals and sensed voltages $V_{DA}$, $V_{DB}$, $I_{SA}$, $I_{SB}$, $V_{SA}$, $V_{SB}$ in the example above.

In use, the amplifier $A_1$ operates to amplify the analogue voltage signal received from the DAC 329 and apply this to the subject S via the cable 761, so that the applied voltage drive signal $V_D$ drives a current signal $I_S$ through the subject S. The voltage drive signal $V_D$, will only be applied if the switch SW is in a closed position and the switch SW can therefore be placed in an open position to isolate the voltage source from the subject S. This may be used if a pair of drive and sense electrodes 113, 115 are being used to sense voltages only, and are not being used to apply a voltage drive signal $V_D$ to the subject S. Isolating the signal generator 117 from the drive electrode 113 removes the unintended return current path(s) that would otherwise be present due to the low output impedance of the amplifier $A_1$, thereby constraining current to flow only between the two selected drive electrodes 113. Other techniques may be used to achieve a similar effect, such as using an amplifier incorporating a high impedance output-disable state.

The current signal $I_S$ being applied to the subject S is detected and amplified using the amplifier $A_2$, with the amplified current signal $I_S$ being returned to the processing system 330, along the cable 753 and via the ADC 328.

Similarly, the sensor 118 operates by having the amplifier $A_3$ amplify the voltage detected at the second electrode 115, returning the amplified analogue sensed voltage signal $V_S$ along the cable 754, to the ADC 327.

The cables 751, 752, 753, 754, 755, 756 may be provided in a number of different configurations depending on the preferred implementation. In one example, each of the cables 751, 752, 753, 754, 755, 756 are provided in a single lead L, although this is not essential, and the cables could be provided in multiple leads, as will be described in more detail below.

Figure 7B:
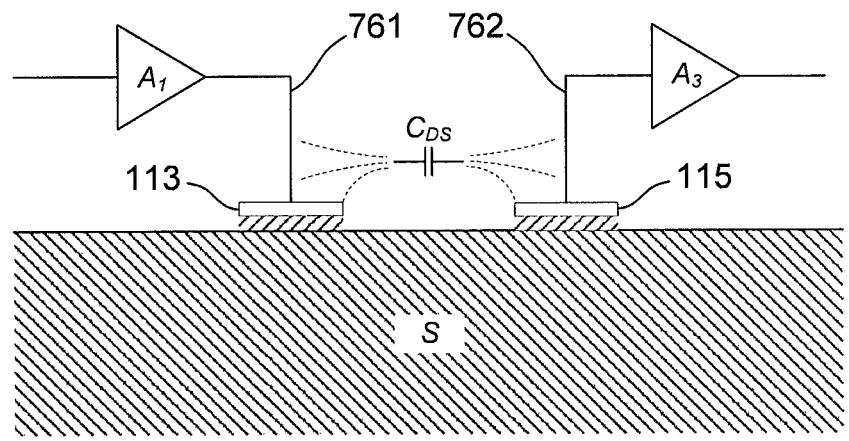
FIG. 7B is a schematic diagram illustrating cross electrode capacitive coupling.

Another potential source of error is caused by cross electrode capacitive coupling. As shown in FIG. 7B, the relative proximity of the electrodes 113, 115 and the corresponding connections 761, 762, results in an effective capacitance $C_{DS}$, between the output of the drive amplifier $A_1$ and the input of the sense amplifier $A_3$. Accordingly, this will cause a parasitic current flow between the amplifiers electrodes $A_1$, $A_3$, which can in turn result in inaccuracies in the measurements, particularly at higher frequencies.

Figure 7C:
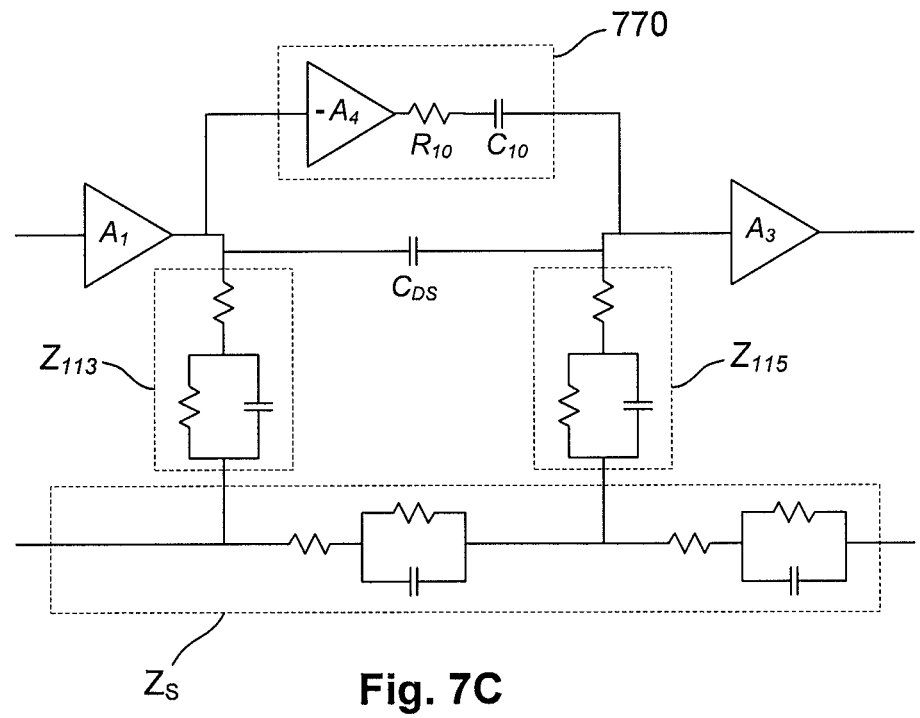
FIG. 7C is a schematic diagram of an example of a cross electrode capacitance cancelling circuit.

To cancel the cross electrode capacitive coupling a cross electrode capacitance cancelling circuit is provided, as shown in FIG. 7C, which shows an equivalent circuit modelling the electrical responsiveness of the electrodes 113, 115 in use.

In this example, the impedances of each electrode 113, 115 and the subject S are represented by respective impedances $Z_{113}$, $Z_{115}$, $Z_S$, formed by respective resistor and capacitor arrangements. The cross electrode capacitance cancelling circuit 770 is coupled to the output of the drive amplifier $A_1$ and the input of the sense amplifier $A_3$, and includes an inverting amplifier $A_4$, having an input coupled to the output of the drive amplifier $A_1$. The output of the inverting amplifier is connected in series via a resistor $R_{10}$ and a capacitor $C_{10}$, to the input of the sense amplifier $A_3$.

In this arrangement any signal output from the drive amplifier $A_1$ will be inverted and then applied to the input of the sense amplifier $A_3$. By selecting appropriate values for the resistor $R_{10}$ and a capacitor $C_{10}$, this allows the inverted signal to have a magnitude equal to the magnitude of any signal resulting from the effective cross electrode capacitance $C_{DS}$.

In one example, the resistance and/or capacitance of the resistor $R_{10}$ and capacitor $C_{10}$ respectively, can be adjusted, through the use of suitable adjustable components, such as a variable resistor or capacitor. This allows the magnitude and/or phase of the inverted signal to be controlled so that it effectively cancels the signal resulting from the effective cross electrode capacitance $C_{DS}$. It will be appreciated that adjustment of the components may be performed during a calibration process, which will typically include the complete electrode unit together with its associated electrodes attached so that all parasitic capacitances are accurately represented.

Accordingly, the cross electrode capacitance cancelling circuit 770 provides an effective negative capacitance between the drive electrode 113 and corresponding sense electrode 115, so that a negative current flow occurs, thereby cancelling the parasitic current. This therefore negates the effect of any capacitive coupling between the drive and sense electrodes 113, 115.

Figure 7D:
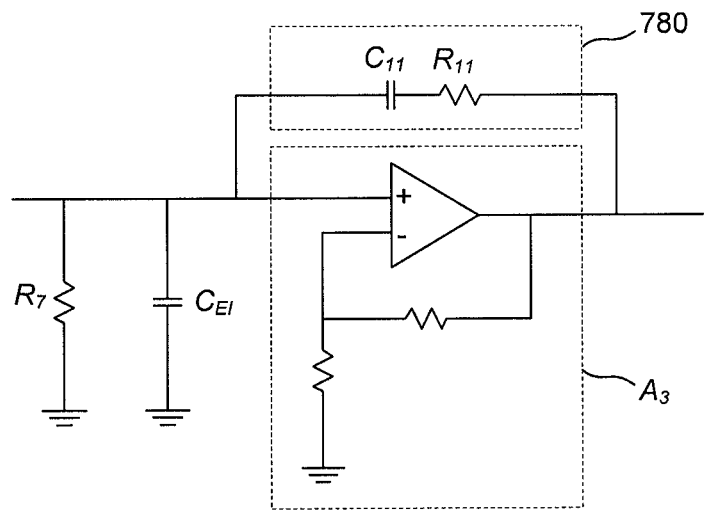
FIG. 7D is a schematic diagram of an example of an input capacitance cancelling circuit.

The electrode system may also include an input capacitance cancelling circuit, an example of which is shown in FIG. 7D.

In use, the sense electrodes 115 can capacitively couple to the environment, which results in an effective input capacitance $C_{EI}$ at the input of the sense amplifier $A_3$. The effective capacitance allows signal leakage from the input of the sense amplifier to ground, thereby reducing the signal available at the amplifier input.

Accordingly, in this example, an input capacitance cancelling circuit 780 is provided which connects the positive amplifier input of the sense amplifier $A_3$ to the output of the sense amplifier, via a resistor $R_{11}$ and a capacitor $C_{11}$. This acts as a positive feedback loop, allowing a proportion of the amplified signal to be returned to the amplifier input. This acts to cancel the reduction in signal at the amplifier input that is caused by the effective input capacitance $C_{EI}$, and therefore provides an effective negative capacitance that cancels the effect of the effective input capacitance $C_{EI}$ at the amplifier input. Again, the input capacitance cancelling circuit requires tuning, which can be achieved during calibration by suitable adjustment of the values of the resistor $R_{11}$ and/or the capacitor $C_{11}$.

As briefly mentioned above, when separate leads 123, 125 are used for the voltage signal $V_S$ and the current signal $I_S$, then inductive coupling between the leads 123, 125 can result in EMFs being induced within the leads 123, 125. The magnitude of the EMF is dependent on the degree of coupling between the leads 123, 125 and hence their physical separation, and also increases in proportion to the frequency and amplitude of the current signal $I_S$.

The EMF induced within the leads 123, 125 results in an effective EMF across the input of the sensor 118. As a result, a component of the sensed voltage signal $V_S$ is due to the induced EMF, which in turn leads to inaccuracies in the determined voltage signal $V_S$ and the current signal $I_S$.

The effect of inductive coupling varies depending on the physical separation of the leads 123, 125. Accordingly, in one example, the effect of inductive coupling between leads can be reduced by physically separating the leads as much as possible. Thus, in one example, the cables 751, 752, 753, 754, 755, 756 are provided in separate physically separated leads. However, a problem with this arrangement is that the amount of inductive coupling will vary depending on the physical lead geometry, which can therefore vary between measurements. As a result, the magnitude of any inductive coupling can vary, making this difficult to account for when analysing the impedance measurements.

An alternative to using physically separate leads for each of the cables 751, 752, 753, 754, 755, 756 is to use a single combined lead L. The lead is formed so that the cables 751, 752, 753, 754, 755, 756 are held in a substantially constant relative physical configuration. In one example, the leads L are formed so as to provide a constant geometric arrangement by twisting each of the respective cables together. However, alternative fabrication techniques could be used such as making the leads from separate un-insulated shielded cables that are over moulded to maintain close contact.

As a result of the constant physical geometry, any EMF induced along the leads 123, 125 is substantially constant, allowing this to be accounted for during a calibration process.

Accordingly, when the measuring device 320 is initially configured, and in particular, when the algorithms are generated for analysing the voltage and current signals $V_S$, $I_S$, to determine impedance measurements, these can include calibration factors that take into account the induced EMF. In particular, during the configuration process, a measuring device 320 can be used to take measurements from reference impedances, with the resulting calculations being used to determine the effect of the induced EMF, allowing this to be subtracted from future measurements.

Figure 8:
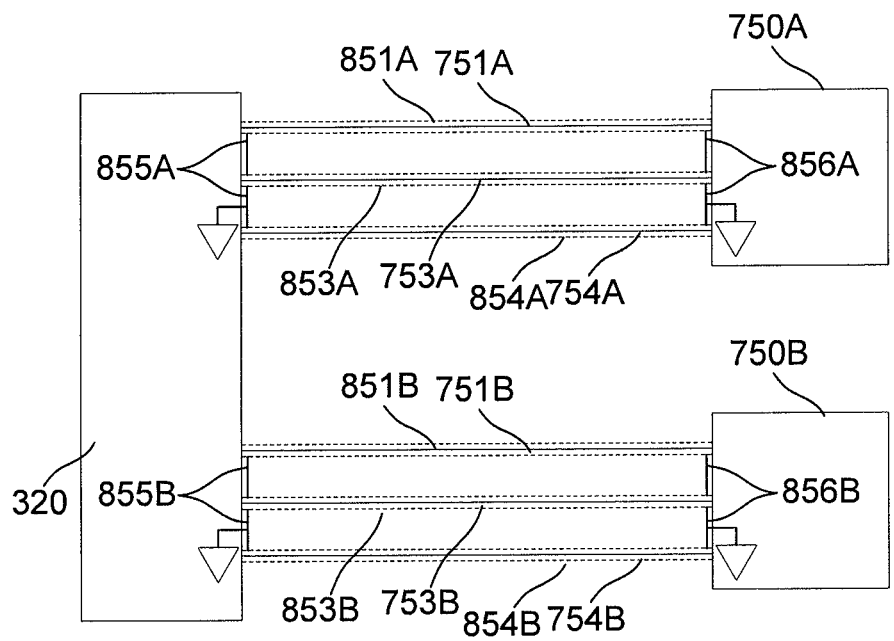
FIG. 8 is a schematic diagram of an example of lead connections between the measuring device and the electrode system of FIG. 7A.

A further issue with the lead arrangement is that of capacitive coupling between the respective cables, as will now be described with respect to FIG. 8. For the purpose of this example, only cables 751, 753, 754 are shown for clarity.

In this example, the measuring device 320 is connected to the PCB's 750A, 750B to provide connections for each of the electrodes 113A, 113B, 115A, 115B. As also shown, each of the cables 751, 753, 754 have respective shielding 851, 853, 854 provided thereon. The shielding is used to help prevent coupling between the respective cables 751, 753, 754. It will therefore be appreciated that the cables 751, 753, 754 are generally formed from a shielded wire core. In practice, the shielded cables may be 50Ω transmission lines, which minimize signal transmission distortion at high frequencies, thereby minimizing errors. In addition to this, the shields 851, 853, 854 are typically interconnected at each end, to a reference voltage such as a ground, via respective connections 855, 856.

The use of shielded and grounded cables in this fashion helps reduce the effect of capacitive coupling, helping to further reduce inaccuracies in obtained measurements.

A further potential issue is that of inductive coupling between the different leads L, as well as capacitive coupling between the subject and the subject and the bed. In this regard, parasitic capacitances allow high frequency currents to bypass the intended current path through the body, resulting in measurement errors. To take this into account, in one example, the leads L for each electrode system can be physically separated as much as possible and/or provided in an arrangement that minimizes lead length in use. An example of an arrangement for achieving this will now be described with respect to FIG. 9.

For the purpose of this example, the measuring system provides four measuring channels, designated by the suffixes A, B, C, D. It will be appreciated that this can be achieved by using a modified version of the measuring device 320 of FIG. 3, in which further ADCs 327, 328 and DACs 329 are provided as briefly described above.

In this example, the subject S is laying on a bed 900, with arms 931, 932 positioned by the subject's side, and the legs 933, 934 resting on a support 940, which incorporates the measuring device 320. The support may be any form of support, but is typically formed from moulded foam, or the like, which arranges the subject with the measuring device 320 positioned substantially between the subject's knees. The measuring device 320 is typically incorporated into the support both to ensure accurate location of the subject relative to the measuring device 320, and also to protect the subject S from damage caused by rubbing or other impact with a housing of the measuring device 320.

By providing a four channel arrangement, this allows a respective electrode system to be mounted to each of the subject's limbs. Thus, as shown, each limb 931, 932, 933, 934 has a respective substrate 760 mounted thereon, to thereby provide a drive and sense electrode 113, 115 on each wrist and ankle. The electrodes 113, 115, are coupled to respective signal generators and sensors mounted on the substrates 750, which are in turn coupled to the measuring device 320 via respective leads LA, LB, LC, LD.

The leads are arranged so that each lead LA, LB, LC, LD extends away from the measuring device 320 in different directions, thereby maximizing the physical separation of the leads and hence helping to reduce any inductive coupling therebetween.

Additionally, the leads LA, LB, LC, LD are preferably adapted to extend perpendicularly from both the measuring device 320 and the subject S, to thereby further reduce the effects of capacitive coupling.

Furthermore, by having the measuring device 320 positioned near the subject's knee, this places the measuring device 320 approximately equi-distant between the subject's wrists and ankles. Thus, by arranging the measuring device 320 towards the lower end of the bed 900, this reduces the length of leads LA, LB, LC, LD needed to place the electrodes on the wrist and ankle of the subject S, whilst maintaining substantially equal lead lengths, which helps further reduce both inductive and capacitive coupling effects. In this regard, the EMF originating from any inductive coupling effect is proportional to the relevant lead length, thereby equalising any effect for the different leads. Similarly, capacitive coupling between the leads (ground) and the subject S, which can create current shunt paths, is also minimized.

The above described arrangement is for the purpose of example only, and it will be appreciated that in practice, any suitable mechanisms for positioning the measuring device 320 in the vicinity of the subject's upper legs (approximately midway between the wrists and ankles) can be used.

Thus, for example, this could involve simply resting the measuring device 320 on the subject's legs, providing a custom built support, or the like.

It will be appreciated that in this arrangement, by having four first electrodes and four second electrodes positioned on the limbs, this allows a range of different limb and/or whole body impedance measurements to be performed.

The electrode configuration shown in FIG. 9 can be used to perform an alternative balancing process, as will now be described with reference to FIGS. 10A and 10B.

Figure 9:
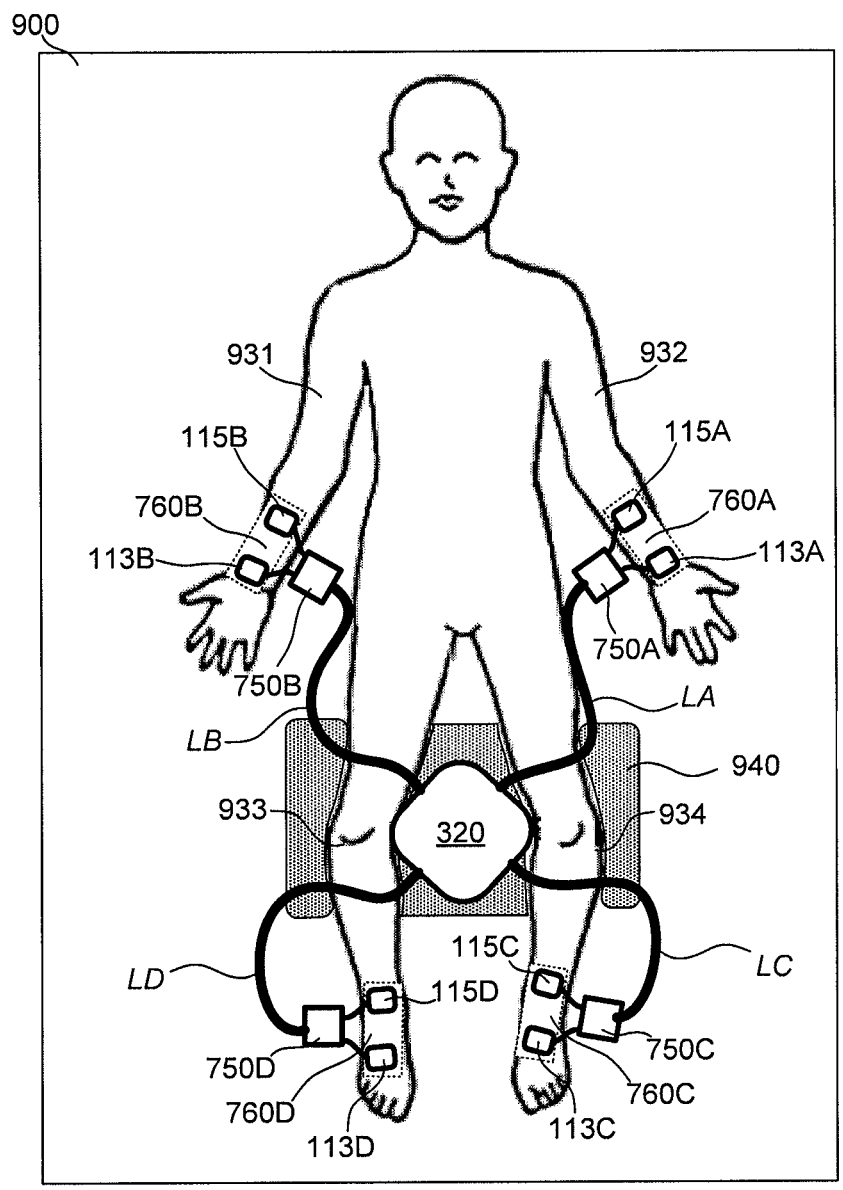
FIG. 9 is a schematic diagram of an example of a lead arrangement.

For the purpose of these examples, the subject S has arms 1031, 1032, legs 1033, 1034 and a torso 1035 and the measuring device 300 (not shown for clarity) is provided in a multi-channel configuration similar to that shown in FIG. 9, with respective pairs of drive and sense electrodes 113A, 115A; 113B, 115B; 113C, 115C; 113D, 115D provided on the wrist and ankles of the subject. In FIGS. 10A and 10B, active electrodes only are shown.

In each example, a drive electrode configuration is used that applies a drive signal to the drive electrodes 113B, 113D, so that the signal passes through the arm 1031, the torso 1035 and the leg 1033, as shown by the dotted line 1040.

In the example of FIG. 10A sense electrodes 115B, 115D provided on the arm 1031 and on the leg 1033 are used to perform the balancing. In contrast, in the arrangement of FIG. 10B, the sense electrodes 115A, 115C provided on the contralateral limbs 1032, 1034 are used to perform balancing. This leads to different effective electrical models for the balancing process, as shown in FIG. 10C. The effective electrical model represents impedances encountered by the drive signal, including impedances $Z_{113B}$, $Z_{113D}$, $Z_{1031}$, $Z_{1035}$, $Z_{1033}$, representing the impedances of the drive electrode impedances 113B, 113D, the arm 1031, the torso 1035 and the leg 1033, respectively.

In the electrode configuration of FIG. 10A, the sense electrodes are provided on the arm 1031 and the leg 1033, so that voltages induced within the subject are effectively sensed at the points between the drive electrodes 113B, 113D and the respective limb 1031, 1033. The sensed voltages measured at the electrodes 115B, 115D are shown at $V_{SB}$ and $V_{SD}$, respectively, and these effectively take into account current flow through the arm 1031, the torso 1035 and the leg 1033.

When performing balancing, the drive signal is controlled to minimise the common mode voltage such that $V_{SB} \approx -V_{SD}$. In this configuration, the effective ground reference voltage $V_R$ is electrically centred between the sensed voltages $V_{SB}$, $V_{SD}$, such that the differences $\Delta V_B$, $\Delta V_D$ between the reference voltage $V_R$ and each sensed voltage $V_{SB}$, $V_{SD}$ is approximately equal $\Delta V_B \approx \Delta V_D$. This therefore takes into account differences in impedances for the drive electrodes 113B, 113D, which typically arise from different contact impedances, so that if one of the electrodes has a significantly higher impedance than the other electrode, the signal applied to the body after the electrodes is still symmetrical with respect to the sense electrodes 115B, 115D.

As the arm impedance of the arm $Z_{1031}$ is generally higher than the torso impedance $Z_{1035}$ and leg impedance $Z_{1033}$, then generally the signal voltage difference across the arm 1031 is approximately equal to that across the torso 1035 and leg 1033 combined. Consequently, the location of the reference voltage $V_R$ does not generally occur at the geometric centre of the subject's body, but rather occurs somewhere near the shoulder region of the subject S. As a result, the subject's body centre voltage Vc is not necessarily minimised by balancing according to the sensed voltages $V_{SB}$, $V_{SD}$ and there can be a significant residual signal voltage V at the centre of the subject's torso 1035, which corresponds to the subject's body centre. Thus, the body centre voltage $V_C = V \neq V_R$. The residual signal voltage will result in current flow due to capacitive coupling between the subject and the environment, such as the bed on which the subject is positioned. This in turn impacts on the accuracy of the impedance measurements.

By contrast, the arrangement shown in FIG. 10B senses the voltages in the subject using the sense electrodes 115A, 115C provided on the contralateral limbs 1032, 1034. As there is no current flow through the contralateral limbs 1032, 1034, the contralateral limbs 1032, 1034 are effectively at the same voltage along their entire length (i.e. isopotential). Accordingly, the sense electrodes 115A, 115C effectively measures the voltages at the point where the torso 1035 joins the arm 1031 and the leg 1033 as also shown in FIG. 10C.

In this instance if the balancing is performed, the reference voltage $V_R$ is electrically centred between the sensed voltages $V_{SA}$, $V_{SC}$, such that the difference $\Delta V_A$, $\Delta V_C$ between the reference voltage $V_R$ and each sensed voltages $V_{SA}$, $V_{SC}$ is approximately equal $\Delta V_A \approx \Delta V_C$. As the voltage induced by the overall drive signal $V_D$ is measured across the torso only, and as the upper and lower torso have similar impedances, the reference voltage $V_R$ is positioned midway along the torso 1035. As the reference voltage is typically set to 0V, this minimises the amplitude of the signal voltage on the torso 1035, as induced by the drive signal, which in turn reduces the effect of capacitive coupling between the subject and the bed.

Accordingly, whilst it will be appreciated that balancing can be performed using the configuration of FIG. 10A, this typically only takes into account variations in electrode impedances of the drive electrodes 113B, 113D. Whilst this will also generally reduce the overall potential of the subject's torso, and hence reduce the effect of parasitic capacitances, it still does not necessarily result in the voltages in the body being balanced symmetrically with respect to the torso. Accordingly, in one example it is preferred to use the electrode configuration shown in FIG. 10B.

Thus, balancing can be performed for a range of different electrode configurations, including sensing voltages on the same limbs to which the voltage drive signals are applied. However, in one example, the balancing is performed by passing signals along a first limb, the torso and a second limb with the voltage signals being measured by different third and fourth limbs. By measuring the voltages on different limbs, this ensures that balancing is performed about the subject's torso which in turn results in reduced effect of capacitive coupling between the subject and the environment.

It will be appreciated that in practice, there will always be some parasitic current flow from the torso even when the centre-body voltage is balanced. This is due to the relatively large physical size of the torso. However, the process of balancing the centre-body voltage attempts to minimise this error and also enables a repeatable reference point to be achieved.

Figure 11:
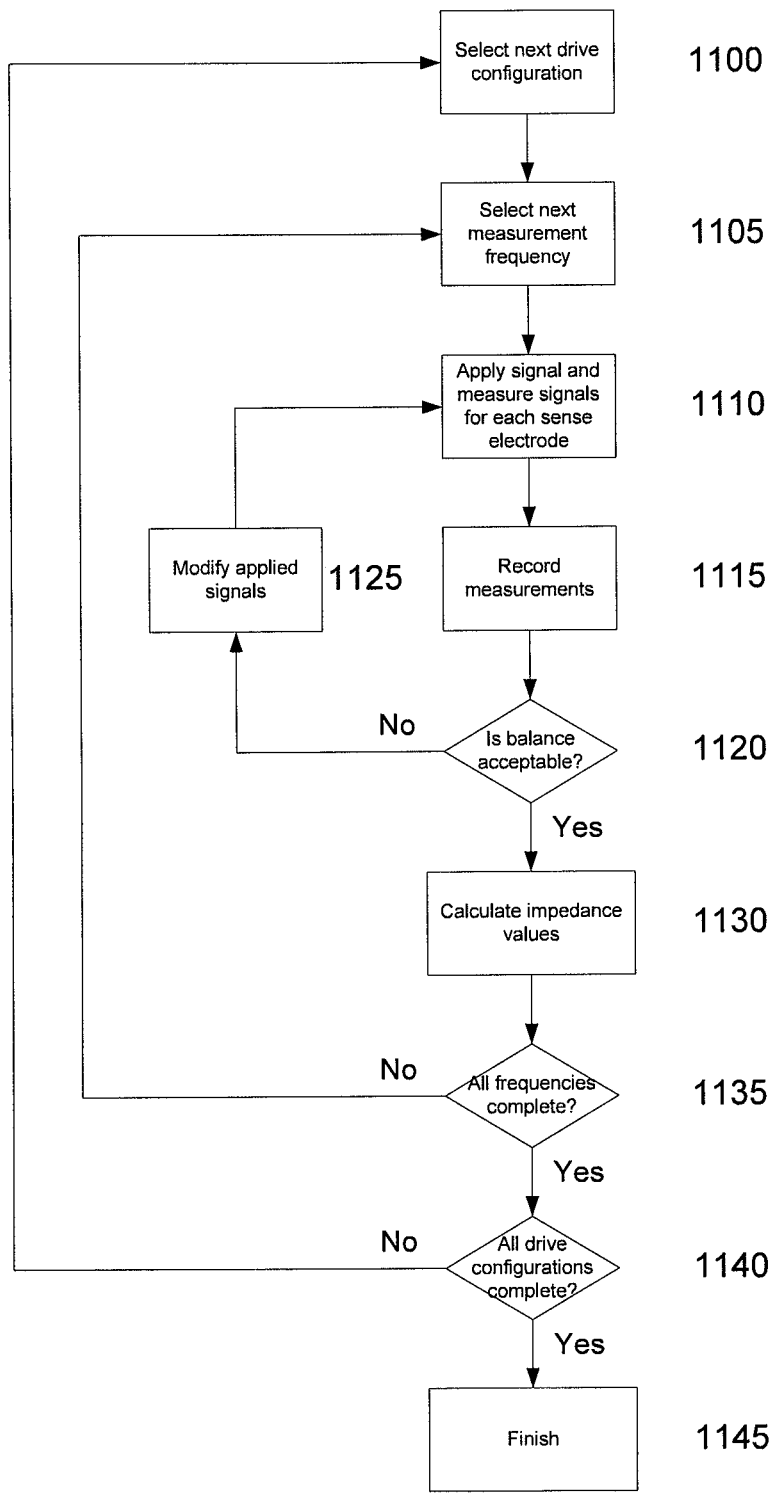

A further example measurement sequence will now be described in more detail with reference to FIG. 11.

For the purpose of this example, it is again assumed that the device is provided in a multi-channel configuration similar to that shown in FIG. 9, with respective pairs of drive and sense electrodes 113A, 115A; 113B, 115B; 113C, 115C; 113D, 115D provided on the wrist and ankles of the subject. In this example, when a measurement process is being performed, a drive electrode configuration is selected at step 1100. This may involve for example selecting the drive electrodes 113B, 113D, although any suitable combination of drive electrodes may be used, depending on the type of impedance measurement to be performed.

At step 1105 a next measurement frequency is selected, with voltage drive signals $V_{DB}$, $V_{DD}$ being applied to the subject at 1110. This allows voltages $V_{SA}$, $V_{SB}$, $V_{SC}$, $V_{SD}$ at each sense electrode 115A, 115B, 115C, 115D to be measured by the respective sensors 118A, 118B, 118C, 118D, and current signals $I_{SA}$, $I_{SB}$, $I_{SC}$, $I_{SD}$, resulting from the voltage drive signals $V_{DB}$, $V_{DD}$ to be measured by the signal generators 117A, 117B, 117C, 117D, with a indication of the sensed voltage signals $V_{SA}$, $V_{SB}$, $V_{SC}$, $V_{SD}$ and current signals $I_{SB}$, $I_{SD}$ being transferred to the measuring device 320.

The indication of each of the signals is then typically stored at step 1115. This information can be recorded for a number of purposes and in general, it is easiest to simply record indication of each of the signals, rather selectively record information based on a measurement protocol.

By recording all signals, including all four sensed current and sensed voltage signals, this also allows a single measurement collection protocol to be performed for a variety of different purposes. The recorded data can then be subsequently analysed in a variety of different manners, depending on the intended measurement to be performed. Thus, for example, recorded data could be analysed to provide information regarding body composition, the presence, absence or degree of oedema, or the like.

At step 1120 the measuring device 320 determines if the balance is acceptable. Thus, for example, if the voltage drive signals $V_{DB}$, $V_{DD}$ are being applied via the electrodes 113B, 113D, the measuring device 320 will select the sensed voltages $V_{SA}$, $V_{SC}$, at the sense electrodes 115A, 115C thereby allowing balancing to be assessed, in a manner similar to that described above. In this instance, an additive voltage $V_{SA}+V_{SC}$ will be determined based on the sensed voltages $V_{SA}$, $V_{SC}$. The additive voltage will be compared to a threshold, and if this is below the threshold, this indicates that the balancing is acceptable.

In the event that the balancing is not acceptable, then the voltage drive signals $V_{DB}$, $V_{DD}$ applied to the subject S are modified at step 1125. The manner in which the signals are adjusted can depend on the preferred implementation. In one example, the adjustment is performed based on the results of the measurements performed at step 1110.

Thus, for example, the sensed voltages $V_{SA}$, $V_{SC}$ can be used to determine a body centre voltage $V_C$. The sensed current signals $I_{SB}$, $I_{SD}$, and voltage drive signals $V_{DB}$, $V_{DD}$, applied via each drive electrode 113B, 113D are used together with the body centre voltage $V_C$ to determine upper and lower impedances $Z_{upper}$, $Z_{lower}$, which represent the impedance of the subject's body and the drive electrodes 113B, 113D on either side of the body centre. The upper and lower impedances $Z_{upper}$, $Z_{lower}$ can then be used to determine the modified signals, based on a preferred current flow through the subject.

An example calculation is shown in more detail below. In this example, the body centre voltage $V_C$ is based on:

$$V_C = (V_{SA} + V_{SC})/2 \tag{1}$$

A current flow through the subject is then determined based on:

$$I = (I_{SB} - I_{SD})/2 \tag{2}$$

where: $I_{SB}$=sensed current flow caused by positive voltage drive signal $V_{DB}$ applied to electrode 113B
$I_{SD}$=sensed current flow caused by negative voltage drive signal $V_{DD}$ applied to electrode 113D This allows an impedance to be determined for the upper and lower portions of the subject, where:

$$Z_{upper} = (V_{DB} - V_C)/I \tag{3}$$

$$Z_{lower} = (V_{DD} - V_C)/I \tag{4}$$

where: $Z_{upper}$=upper body and drive electrode 113B impedance
$Z_{lower}$=lower body and drive electrode 113D impedance Following this, an ideal current value $I_{ideal}$ (typically set to 90 µA RMS to ensure subject safety) is used to determine predicted voltage drive signals that will result in a balanced measurement arrangement, using the equation:

$$V_{DB\,predicted} = I_{ideal} \times Z_{upper} \tag{5}$$

$$V_{DD\,predicted} = I_{ideal} \times Z_{lower} \tag{6}$$

where: $V_{DB\,predicted}$=predicted ideal voltage drive signal for electrode 113B
$V_{DD\,predicted}$=predicted ideal voltage drive signal for electrode 113D Thus, it will be appreciated that in this example, the modified voltage drive signals applied to the subject S are the predicted ideal voltage $V_{DB\,predicted}$, $V_{DD\,predicted}$. The above described example calculation is for the purpose of example only, and alternative calculations may be used.

In one example, the calculations are performed on the basis of the magnitude of the signals only. This is because the magnitude of the voltage at the body centre will have the greatest impact on leakage current between the subject and the environment.

However, balancing the magnitude only can lead to phase differences between the drive signals, which in turn can lead to the body centre voltage $V_C$ including an imaginary component. Examples of this will now be described with reference to FIGS. 12A to 12F.

Figure 12A:
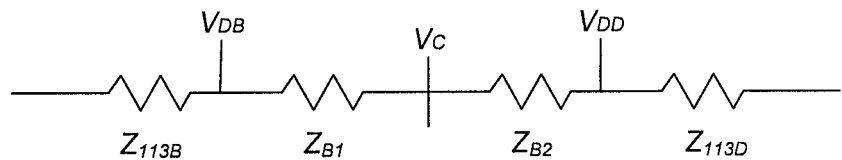
FIG. 12A is a schematic diagram of an effective electrical model of the body.
Figure 12B:
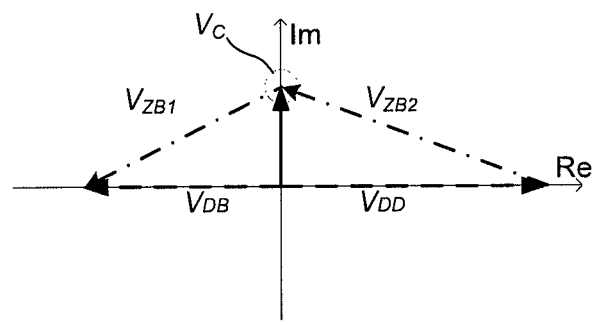
FIG. 12B is a schematic diagram of the complex voltages for the electrical model of FIG. 12A when the voltage is balanced based on the voltage magnitude only.

In the example of FIG. 12B, the voltages are shown based on the equivalent circuit of FIG. 12A, in which the subject is represented by body impedances $Z_{B1}$, $Z_{B2}$, positioned either side of the body centre. Electrode impedances are shown as part of the body impedances, with drive voltages $V_{DB}$, $V_{DD}$ being applied directly to the body impedances $Z_{B1}$, $Z_{B2}$ as shown.

As shown in FIG. 12B, if drive voltages $V_{DB}$, $V_{DD}$ including only real components are applied, then the complex nature of the body impedances $Z_{B1}$, $Z_{B2}$, will result in a phase shift in the voltages $V_{ZB1}$, $V_{ZB2}$ across the body impedances $Z_{B1}$, $Z_{B2}$. As a result, there exists an imaginary component to the body centre voltage. This residual complex component to the body centre voltage can lead to a leakage current from the body as well as extra common mode error in the sensed voltage signals, thereby making it undesirable.

Figure 12C:
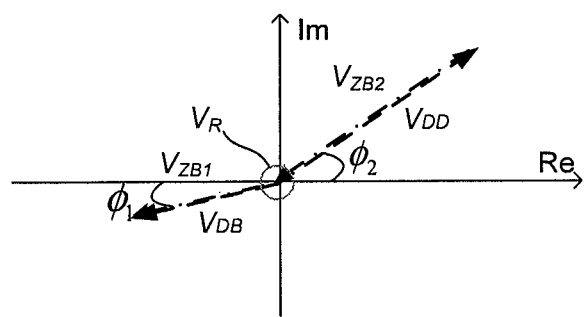
FIG. 12C is a schematic diagram of the complex voltages for the electrical model of FIG. 12A when the voltage is balanced based on the voltage magnitude and phase.

However, in the example of FIG. 12C, if drive voltages $V_{DB}$, $V_{DD}$ include imaginary components, representing a respective phase difference between the applied signal, then this ensures that the phase of the voltages at the body centre are matched. This ensures that the magnitude of the body centre voltage $V_C$, is minimised both in respect of the real and imaginary components.

Figure 12D:
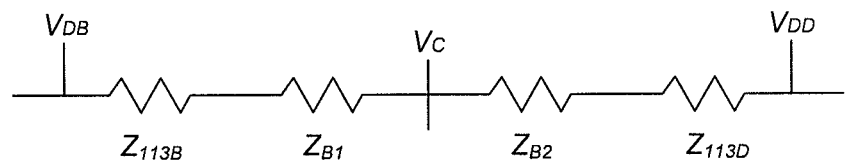
FIG. 12D is a schematic diagram of an effective electrical model of the body.
Figure 12E:
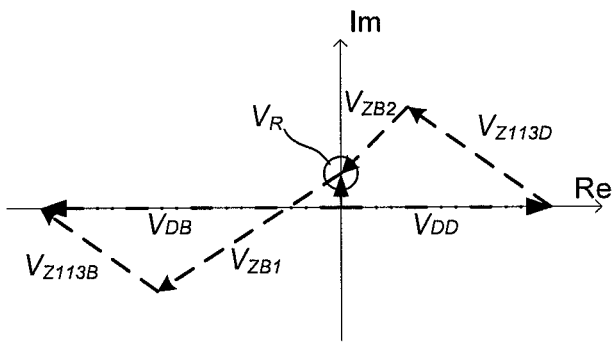
FIG. 12E is a schematic diagram of the complex voltages for the electrical model of FIG. 12D when the voltage is balanced based on the voltage magnitude only; and, FIG. 12F is a schematic diagram of the complex voltages for the electrical model of FIG. 12D when the voltage is balanced based on the voltage magnitude and phase.
Figure 12F:
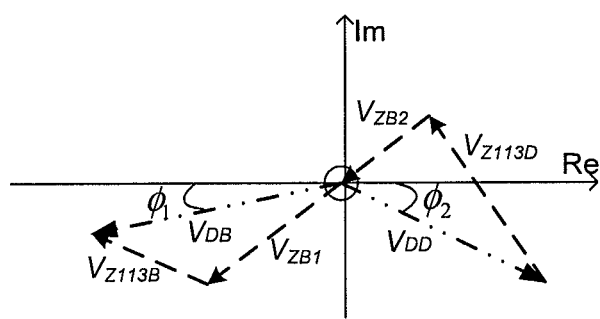

An example of this scenario in which electrode impedances $Z_{113B}$, $Z_{113D}$, for the drive electrodes 113B, 113D are taken into account are shown in FIGS. 12D to 12F. Again, it can be seen that introducing a suitable phase change in the drive voltage signals $V_{DB}$, $V_{DD}$ can result in a body centre voltage that is balanced in respect of both real and imaginary components.

Accordingly, in another example, the balancing procedure can be performed by representing the voltage signals as complex numbers representing both the magnitude and phase of the voltage signals, and by using a complex representation of the impedance. In this instance, this ensures that both the magnitude and phase of the voltage signals are balanced, thereby ensuring a minimal body centre voltage.

In general, when modifying the phase of the applied voltage drive signals, the half body impedances are assumed to have symmetrical phase shift relative to the drive. Thus an impedance vector difference of 20° will be resolved as +10° at one drive and −10° at the second drive. By keeping the drives as symmetrical as possible, any leakage current induced by the capacitance of each limb is equalised and thus halved. However, this is not essential, and any method of modifying the phase may be used.

Following determination of the modified voltage drive signals, steps 1110 to 1120 are repeated using the modified voltage drive signals, with further modified voltage drive signals being calculated until an acceptable balance situation results. It will be appreciated that the number of iterations required to reach an acceptable balance will depend on how close to a balanced situation the initial drive signals are.

Whilst, voltage drive signals $V_{DB}$, $V_{DD}$ having equal magnitudes and/or phase could initially be applied, so that $V_{DB}=-V_{DD}$, this can lead to a relatively large number of different modified signals being tried until a balance condition is reached. As the frequency of the voltage drive signal changes, the body impedance will also change. Accordingly, in one example, for a given frequency $f_{i+1}$ the initially applied drive signals $V_{DB}(f_{i+1})$, $V_{DD}(f_{i+1})$ are calculated based on the signals $V_{DB\,predicted}(f_i)$, $V_{DD\,predicted}(f_i)$ determined for a previous frequency $f_i$. Thus, the signals $V_{DB\,predicted}(f_i)$, $V_{DD\,predicted}(f_i)$ are used to calculate $Z_{upper}(f_i)$, $Z_{lower}(f_i)$. The complex representation of $Z_{upper}(f_i)$, $Z_{lower}(f_i)$ are used to determine $Z_{upper}(f_{i+1})$, $Z_{lower}(f_{i+1})$ which are in turn used together with the ideal current to calculate initial values for $V_{DB\,predicted}(f_{i+1})$, $V_{DD\,predicted}(f_{i+1})$. These values are used as the initial signals applied to the subject at step 1110 for the next frequency $f_{i+1}$.

By using the balance condition determined for a previous frequency as the initial starting point for the balancing algorithm at a next frequency, this significantly reduces the number of iterations required to achieve a balance condition in which $V_C \approx 0$. Typically, using this technique, the balance condition can be determined to less than 0.1% error within three iterations.

Thus, the first iteration with the voltage drive signals $V_{DB}(f_{i+1})$, $V_{DD}(f_{i+1})$ based on the previously determined modified signals $V_{DB\,predicted}(f_i)$, $V_{DD\,predicted}(f_i)$ typically results in a body centre voltage $V_C$ that is within 10% of that required. Thus, the common mode signal voltage at body centre has a magnitude that is approximately 10% of the signal voltage sensed between $V_{SA}$, $V_{SC}$. For the second iteration, the voltage drive signals $V_{DB}$, $V_{DD}$ can be set to achieve $V_C$ to within 1.0% and the third iteration achieves 0.1% error.

This can therefore dramatically reduce the time required for a complete frequency sweep. The measurement time can be further optimised by taking into account the amplitude of noise on the measurements. Measurement time is dependent on the number of samples required to achieve the desired accuracy. Increased noise requires more samples, which takes more time. Therefore, if the number of samples is optimised according to measured noise level, measurement times can be further reduced (from what would otherwise need to be a default sample number).

Once a balance is achieved, the measurements recorded at step 1115 can be used to calculate impedance values at step 1130. It is then assessed whether all frequencies are complete and if not the process returns to step 1105 to select a next measurement frequency. Otherwise it is determined if all drive configurations are complete and if not the process returns to step 1100 to allow an alternative drive configuration to be selected.

Otherwise the process finishes at step 1145, allowing any determined impedance values to be provided to the processing system 310 for subsequent analysis.

Persons skilled in the art will appreciate that numerous variations and modifications will become apparent. All such variations and modifications which become apparent to persons skilled in the art, should be considered to fall within the spirit and scope that the invention broadly appearing before described.

For example, two different approaches to balancing are described above. In the first example, the balancing is performed using sense electrodes attached to the same limbs as the drive electrodes, whereas in the second example, the sense electrodes used for balancing are attached to contralateral limbs. In one example, sense and drive electrode are provided on all limbs, allowing balancing to be performed in a similar manner using any suitable combination of drive and sense electrodes. The electrode combinations used may depend on the impedance measurement being performed.

Additionally features from different examples above may be used interchangeably or in conjunction, where appropriate. Thus, for example, a range of different techniques are described for minimising errors and these can be used independently of each other, or in conjunction, depending on the particular implementation.

Furthermore, whilst the above examples have focussed on a subject S such as a human, it will be appreciated that the measuring device and techniques described above can be used with any animal, including but not limited to, primates, livestock, performance animals, such as race horses, or the like.

The above described processes can be used for diagnosing the presence, absence or degree of a range of conditions and illnesses, including, but not limited to oedema, lymphoedema, body composition, or the like.

The invention claimed is:

1. An apparatus for use in performing impedance measurements on a subject, wherein the apparatus includes a processing system for:
   a) causing a first signal to be applied to the subject, the first signal being voltage drive signals to be applied to the subject via first electrodes
   b) determining sensed current signals caused by the voltage drive signals;
   c) determining an indication of a second signal measured across the subject, the indication of the second signal being a body centre voltage derived from sensed voltages measured via respective second electrodes;
   d) using the indication of the second signal to determine if an unacceptable imbalance exists; and,
   e) if an unacceptable imbalance exists:
   i) determining a modified first signal in accordance with the imbalance by:
   determining upper and lower impedances for the subject using the sensed current signals, the voltage drive signals, and the body centre voltage; and
   determining modified voltage drive signals using the upper and lower impedances and an ideal current signal indication; and,
   ii) causing the modified first signal to be applied to the subject to thereby allow at least one impedance measurement to be performed.

2. The apparatus according to claim 1, wherein the processing system is for:
   a) comparing the second signal to a threshold; and,
   b) determining if an unacceptable imbalance exists depending on the results of the comparison.

3. The apparatus according to claim 1, wherein the second signal includes voltages sensed at respective second electrodes, and wherein the processing system is for:
   a) determining the voltage sensed at each of the second electrodes;
   b) determining an additive voltage; and,
   c) determining the imbalance using the additive voltage.

4. The apparatus according to claim 3, wherein the additive voltage is a common mode signal.

5. The apparatus according to claim 1, wherein the processing system is for determining the modified first signal so as to reduce the imbalance.

6. The apparatus according to claim 5, wherein first signals are applied to the subject via at least two first electrodes, and wherein the processing system is for modifying the first signal by modifying at least one of a phase and a magnitude of at least one first signal applied to at least one of the first electrodes.

7. The apparatus according to claim 1, wherein:
   a) the first signal is applied via first electrodes coupled to first and second limbs of the subject; and,
   b) the second signal is sensed via second electrodes coupled to third and fourth limbs of the subject, the third and fourth limbs being different to the first and second limbs.

8. The apparatus according to claim 1, wherein the processing system is for:
   a) causing the first signal to be applied via first electrodes;
   b) determining indications of second signals sensed at each of a number of second electrodes;
   c) selecting second signals sensed at selected ones of the second electrodes; and,
   d) determining any imbalance using the selected second signals.

9. The apparatus according to claim 1, wherein the first signal includes voltages applied to the subject using first electrodes and the second signal includes voltages sensed at respective second electrodes.

10. The apparatus according to claim 1, wherein the processing system is for performing an impedance measurement by:
    a) determining a sensed current caused by applying the first signal to the subject;
    b) determining a sensed voltage across the subject; and,
    c) determining an impedance parameter using the sensed current and voltage.

11. The apparatus according to claim 1, wherein the processing system is for:
    a) determining a sensed current caused by applying the first signal to the subject;
    b) comparing the sensed current to a threshold; and,
    c) selectively halting the impedance measurement process depending on the results of the comparison.

12. The apparatus according to claim 1, wherein the processing system is for:
    a) determining a sensed current caused by applying the first signal to the subject; and,
    b) using the sensed current in determining the modified first signal.

13. The apparatus according to claim 1, wherein the processing system is for:
    a) causing a first signal to be applied to the subject at a first frequency;
    b) determining an indication of a second signal measured across the subject;
    c) using the indication of the second signal to determine any imbalance;
    d) if no unacceptable imbalance exists, using at least the indication of the second signal to determine at least one impedance value;
    e) if an unacceptable imbalance exists:
    i) determining a modified first signal in accordance with the imbalance;
    ii) causing the modified first signal to be applied to the subject;
    iii) determining an indication of a modified second signal measured across the subject; and
    iv) repeating steps c) to e) for the indication of the modified second signal;
    f) repeating steps a) to e) for at least one second frequency.

14. The apparatus according to claim 1, wherein the voltage drive signals include first and second voltage drive signals applied to the subject via respective first electrodes, the first voltage drive signal having a first magnitude and first phase, and the second voltage drive signal having a second magnitude and second phase and wherein the processing system is for determining the modified voltage drive signals by modifying at least one of:
  a) the first phase;
  b) the first magnitude;
  c) the second phase; and,
  d) the second magnitude.

15. The apparatus according to claim 1, wherein the processing system is for:
  a) causing the modified voltage drive signals to be applied to the subject;
  b) determining sensed voltages measured via respective second electrodes;
  c) determining if an unacceptable imbalance exists using the sensed voltages; and,
  d) if an unacceptable imbalance exists:
    i) determining further modified voltage drive signals; and,
    ii) repeating steps (a) to (d) until any imbalance is acceptable.

16. The apparatus according to claim 1, wherein the processing system is for performing impedance measurements at multiple frequencies, in turn.

17. The apparatus according to claim 16, wherein the processing system is for:
  a) for a first frequency:
    i) determining a modified first signal that results in an acceptable imbalance; and,
    ii) causing an impedance measurement to be performed using the modified first signal; and,
  b) for a second frequency:
    i) causing a first signal to be applied to the subject, the first signal being based on the modified first signal determined for the first frequency; and,
    ii) determining if an unacceptable imbalance exists.

18. The apparatus according to claim 17, wherein the processing system is for:
  a) for a first frequency:
    i) causing first and second voltage drive signals to be applied to the subject via respective first electrodes;
    ii) determining modified first and second voltage drive signals that result in an acceptable imbalance, the first voltage drive signal having a first magnitude and first phase, and the second voltage drive signal having a second magnitude and second phase; and,
  b) for a second frequency:
    i) causing first and second voltage drive signals to be applied to the subject, the first voltage drive signal having the first magnitude and the first phase, and the second voltage drive signal having the second magnitude and the second phase; and,
    ii) determining if an unacceptable imbalance exists.

19. The apparatus according to claim 1, wherein the processing system is for:
  a) generating control signals;
  b) transferring the control signals to at least one signal generator thereby causing the first signal to be applied to the subject;
  c) receiving an indication of the one or more signals applied to the subject from the at least one signal generator;
  d) receiving an indication of one or more second signals measured across the subject from at least one sensor; and,
  e) performing at least preliminary processing of the indications to thereby allow impedance values to be determined.

20. The apparatus according to claim 1, wherein the apparatus includes a differential amplifier for amplifying second signals measured at each of two second electrodes.

21. The apparatus according to claim 20, wherein the differential amplifier generates at least one of:
  a) a differential voltage indicative of the voltage measured at the second electrodes; and,
  b) a common mode signal indicative of any imbalance.

22. The apparatus according to claim 1, wherein the apparatus includes at least one signal generator for applying the first signal to the subject via a first electrode.

23. The apparatus according to claim 22, wherein each signal generator is for:
  a) receiving one or more control signals from the processing system; and,
  b) amplifying the control signals to thereby generate the first signal.

24. The apparatus according to claim 22, wherein each signal generator is for:
  a) determining a sensed current caused by applying the first signal to the subject; and,
  b) providing an indication of the sensed current to the processing system.

25. The apparatus according to claim 22, wherein the apparatus includes at least two signal generators, each signal generator being for connection to a respective first electrode.

26. The apparatus according to claim 22, wherein the apparatus includes at least one sensor for measuring the second signal via second electrodes.

27. The apparatus according to claim 26, wherein the apparatus includes at least two sensors, each sensor being for connection to a respective second electrode.

28. The apparatus according to claim 1, wherein the apparatus includes a number of electrode systems, and wherein each electrode system includes:
  a) a sensor; and,
  b) a signal generator.

29. The apparatus according to claim 28, wherein electrode system includes:
  a) a first substrate having the signal generator and sensor mounted thereon; and,
  b) a second substrate having at least two conductive pads mounted thereon, the conductive pads forming a first and a second electrode for coupling the signal generator and the sensor to a subject in use.

30. The apparatus according to claim 28, wherein the electrode system includes a capacitive cancelling circuit for cancelling capacitive coupling between the first and second electrodes.

31. The apparatus according to claim 30, wherein the capacitive cancelling circuit includes an inverting amplifier for coupling a signal generator output to a sensor input.

32. The apparatus according to claim 31, wherein the inverting amplifier applies a capacitive cancelling signal to the sensor input to thereby cancel any effective capacitance between the first electrode and the second electrode.

33. The apparatus according to claim 31, wherein an inverting amplifier output is coupled to the sensor input via at least one of:
  a) a resistor;
  b) a capacitor; and,
  c) an inductor.

34. The apparatus according to claim 33, wherein at least one of a resistor and capacitor are adjustable, thereby allowing a capacitive cancelling signal applied to the sensor input to be controlled.

35. The apparatus according to claim 28, wherein the electrode system includes an input capacitance cancelling circuit for cancelling an effective input capacitance at a sensor input.

36. The apparatus according to claim 28, wherein the electrode system includes a feedback loop for connecting a sensor output to the sensor input.

37. The apparatus according to claim 36, wherein the feedback loop includes at least one of:
   a) a resistor;
   b) a capacitor; and,
   c) an inductor.

38. The apparatus according to claim 37, wherein at least one of a resistor and capacitor are adjustable, thereby allowing a current flow from the sensor output to the sensor input to be controlled.

39. The apparatus according to claim 37, wherein the feedback loop applies an input capacitance cancelling signal to the sensor input to thereby cancel any effective capacitance at the sensor input.

40. The apparatus according to claim 1, wherein the apparatus includes:
   a) a number of electrode systems, and wherein each electrode system includes a signal generator and sensor; and,
   b) at number of leads for connecting the measuring device to the electrode systems, each lead including:
      i) at least two connections for connecting the measuring device and the signal generator, and the measuring device and the sensor; and,
      ii) a shield for each of the at least two connections, the shields being electrically connected, and electrically connected to a reference voltage in each of the measuring device and the electrode system.

41. The apparatus according to claim 40, wherein the apparatus includes:
   a) at least two electrode systems, each electrode system including:
      i) a signal generator for applying a first signal to the subject;
      ii) a sensor for sensing a second signal across the subject;
      iii) a first electrode for coupling the signal generator to the subject; and,
      iv) a second electrode for coupling the sensor to the subject; and,
   b) a measuring device for controlling the electrode systems to allow impedance measurements to be performed; and,
   c) at least two leads for connecting the measuring device to the electrode systems.

42. The apparatus according to claim 41, wherein the leads are arranged in use to at least one of:
   i) extend from the measuring device in different directions to thereby reduce inductive coupling therebetween; and,
   ii) minimise the lead length.

43. The apparatus according to claim 1, wherein the apparatus includes an interface for coupling the processing system to a computer system, the processing system being for:
   a) generating control signals in accordance with commands received from the computer system; and,
   b) providing data indicative of measured impedance values to the computer system to allow impedance values to be determined.

44. The apparatus according to claim 1, wherein the first signal is includes two first signals applied to the subject via at least two first electrodes, and the second signal includes two second signals sensed at two second electrodes.

45. A method for use in performing impedance measurements on a subject, wherein the method includes, in a processing system:
   a) causing a first signal to be applied to the subject, the first signal being voltage drive signals to be applied to the subject via first electrodes
   b) determining sensed current signals caused by the voltage drive signals;
   c) determining an indication of a second signal measured across the subject, the indication of the second signal being a body centre voltage derived from sensed voltages measured via respective second electrodes;
   d) using the indication of the second signal to determine any imbalance; and,
   e) if an unacceptable imbalance exists:
   i) determining a modified first signal in accordance with the imbalance by:
      determining upper and lower impedances for the subject using the sensed current signals, the voltage drive signals, and the body centre voltage; and
      determining modified voltage drive signals using the upper and lower impedances and an ideal current signal indication; and,
   ii) causing the modified first signal to be applied to the subject to thereby allow at least one impedance measurement to be performed.

* * * * *